US011857785B2

(12) United States Patent
Pearce et al.

(10) Patent No.: US 11,857,785 B2
(45) Date of Patent: Jan. 2, 2024

(54) SYSTEMS, METHODS AND DEVICES FOR ELECTRICAL STIMULATION THERAPY

(71) Applicant: Theragen, Inc., Manassas, VA (US)

(72) Inventors: Richard H. Pearce, Cary, NC (US); Jon Christopher McAuliffe, Jacksonville, FL (US)

(73) Assignee: Theragen, Inc., Manassas, VA (US)

( * ) Notice: Subject to any disclaimer, the term of this patent is extended or adjusted under 35 U.S.C. 154(b) by 0 days.

(21) Appl. No.: 17/887,661

(22) Filed: Aug. 15, 2022

(65) Prior Publication Data

US 2022/0387783 A1 Dec. 8, 2022

Related U.S. Application Data

(63) Continuation of application No. 17/506,851, filed on Oct. 21, 2021, now Pat. No. 11,426,574.
(Continued)

(51) Int. Cl.
*A61N 1/36* (2006.01)
*A61N 1/04* (2006.01)
(Continued)

(52) U.S. Cl.
CPC ........ *A61N 1/36031* (2017.08); *A61B 5/4833* (2013.01); *A61N 1/0464* (2013.01); *A61N 1/0468* (2013.01); *A61N 1/0492* (2013.01); *A61N 1/326* (2013.01); *A61N 1/36034* (2017.08)

(58) Field of Classification Search
CPC ................ A61N 1/0468; A61N 1/0492; A61N 1/36031; A61N 1/36034
See application file for complete search history.

(56) References Cited

U.S. PATENT DOCUMENTS 4,315,503 A 2/1982 Ryaby et al.
4,432,361 A 2/1984 Christensen et al.
(Continued)

FOREIGN PATENT DOCUMENTS

EP 3459453 B1 5/2021

OTHER PUBLICATIONS

Orthofix Wins 2017 Spine Technology Award for STIM onTrack Mobile App, Oct. 25, 2017, 3 pages.
(Continued)

*Primary Examiner* — Amanda K Hulbert
*Assistant Examiner* — Philip C Edwards
(74) *Attorney, Agent, or Firm* — Farber LLC

(57) ABSTRACT

Systems, devices and methods are provided for transcutaneously delivering energy impulses to bodily tissues for therapeutic purposes, such as for enhancing the body's bone healing process in spinal fusion patients. A therapeutic stimulator system comprises a housing for an energy source and a signal generator. The system further includes one or more electrodes coupled to the signal generator. A processor is coupled to the housing and configured to determine usage levels of the signal generator and/or motion data of the housing. The system may include a mobile device that allows the patient to input user status data, such as pain levels, and compare the user status data with the usage levels and/or the motion data, thereby improving patient compliance with a prescribed therapy regimen.

19 Claims, 19 Drawing Sheets

Related U.S. Application Data

(60) Provisional application No. 63/146,196, filed on Feb. 5, 2021.

(51) Int. Cl.
*A61N 1/32* (2006.01)
*A61B 5/00* (2006.01)

(56) References Cited

U.S. PATENT DOCUMENTS

| | | | |
|---|---|---|---|
| 4,467,808 A | 8/1984 | Brighton et al. | |
| 4,467,809 A | 8/1984 | Brighton | |
| 4,509,520 A | 4/1985 | Dugot | |
| 4,548,208 A | 10/1985 | Niemi | |
| 4,556,051 A | 12/1985 | Maurer | |
| D290,095 S | 6/1987 | Montalbano et al. | |
| 4,993,413 A | 2/1991 | McLeod et al. | |
| 4,998,532 A | 3/1991 | Griffith | |
| 5,014,699 A | 5/1991 | Pollack et al. | |
| 5,269,747 A | 12/1993 | Erikson et al. | |
| 5,273,033 A | 12/1993 | Hoffman | |
| 5,324,314 A | 6/1994 | Boetzkes | |
| 5,374,283 A | 12/1994 | Flick | |
| 5,397,338 A | 3/1995 | Grey et al. | |
| 5,401,233 A | 3/1995 | Erikson et al. | |
| 5,413,596 A | 5/1995 | Kronberg | |
| 5,743,844 A | 4/1998 | Tepper et al. | |
| 5,792,209 A | 8/1998 | Varner | |
| 6,564,103 B2 | 5/2003 | Fischer et al. | |
| 6,584,358 B2 | 6/2003 | Carter et al. | |
| 6,675,048 B2 | 1/2004 | McGraw et al. | |
| 6,760,627 B2 | 7/2004 | Carter et al. | |
| 6,792,315 B2 | 9/2004 | Carter et al. | |
| 6,853,863 B2 | 2/2005 | Carter et al. | |
| 6,937,905 B2 | 8/2005 | Carroll et al. | |
| 6,988,005 B2 | 1/2006 | McGraw et al. | |
| 7,117,034 B2 | 10/2006 | Kronberg | |
| 7,158,835 B2 | 1/2007 | Brighton et al. | |
| 7,167,753 B2 | 1/2007 | Brighton et al. | |
| D544,604 S | 6/2007 | Culhane | |
| 7,465,269 B2 | 12/2008 | Culhane | |
| 7,747,332 B2 | 6/2010 | McGraw et al. | |
| 7,758,527 B2 | 7/2010 | Gilmour et al. | |
| 8,070,703 B2 | 12/2011 | Skahan et al. | |
| 8,082,038 B2 | 12/2011 | Simon et al. | |
| RE43,374 E | 5/2012 | Kronberg | |
| 8,454,543 B2 | 6/2013 | Skahan et al. | |
| 8,496,570 B2 | 7/2013 | Culhane | |
| 8,630,714 B1 | 1/2014 | Webb | |
| 8,744,803 B2 | 6/2014 | Park et al. | |
| 8,936,560 B2 | 1/2015 | Lunau et al. | |
| 8,958,883 B2 | 2/2015 | Mueller et al. | |
| 9,114,257 B2 | 8/2015 | Helfer et al. | |
| 9,198,792 B2 | 12/2015 | Skahan et al. | |
| 9,283,371 B2 | 3/2016 | Duncan | |
| 9,669,212 B2 | 6/2017 | Mueller et al. | |
| 9,672,754 B2 | 6/2017 | Yuen et al. | |
| 9,710,607 B2 | 7/2017 | Ramdas et al. | |
| 9,782,122 B1 | 10/2017 | Pulliam et al. | |
| 9,789,308 B2 | 10/2017 | Southwell et al. | |
| 9,875,340 B2 | 1/2018 | Sharma | |
| 10,080,892 B2 | 9/2018 | Southwell et al. | |
| 10,179,239 B2 | 1/2019 | Sharma | |
| 10,195,424 B2 | 2/2019 | Ahmed | |
| 10,195,430 B2 | 2/2019 | Helfer et al. | |
| 10,328,260 B2 | 6/2019 | Mueller et al. | |
| 11,395,919 B1* | 7/2022 | Pearce | A61N 1/0492 |
| 2002/0068961 A1 | 6/2002 | Fischer et al. | |
| 2005/0278001 A1 | 12/2005 | Qin | |
| 2005/0283204 A1 | 12/2005 | Buhlmann et al. | |
| 2005/0283206 A1 | 12/2005 | Hunt et al. | |
| 2006/0030896 A1 | 2/2006 | Simon et al. | |
| 2009/0030476 A1 | 1/2009 | Hargrove | |
| 2011/0288611 A1 | 11/2011 | Lunau et al. | |
| 2011/0319947 A1 | 12/2011 | Chun et al. | |
| 2012/0035683 A1 | 2/2012 | Simon et al. | |
| 2012/0095522 A1 | 4/2012 | Simon et al. | |
| 2012/0221073 A1 | 8/2012 | Southwell et al. | |
| 2012/0253236 A1 | 10/2012 | Snow et al. | |
| 2012/0316482 A1 | 12/2012 | Karim | |
| 2013/0289652 A1 | 10/2013 | Skelton et al. | |
| 2014/0073836 A1 | 3/2014 | Johnson et al. | |
| 2014/0222102 A1 | 8/2014 | Lemus et al. | |
| 2014/0296934 A1* | 10/2014 | Gozani | A61B 5/0531 607/46 |
| 2014/0296935 A1* | 10/2014 | Ferree | A61N 1/3603 607/46 |
| 2014/0330342 A1 | 11/2014 | Lemus et al. | |
| 2015/0088224 A1 | 3/2015 | Goldwasser et al. | |
| 2015/0360030 A1* | 12/2015 | Cartledge | A61N 1/0456 607/136 |
| 2016/0007934 A1 | 1/2016 | Arnold | |
| 2016/0213924 A1 | 7/2016 | Coleman | |
| 2016/0235981 A1 | 8/2016 | Southwell et al. | |
| 2016/0339523 A1 | 11/2016 | Davis et al. | |
| 2017/0007830 A1 | 1/2017 | Yu et al. | |
| 2017/0224990 A1* | 8/2017 | Goldwasser | A61N 1/0476 |
| 2017/0242965 A1 | 8/2017 | Simon | |
| 2018/0140835 A1* | 5/2018 | Sharma | G16H 10/60 |
| 2019/0001129 A1 | 1/2019 | Rosenbluth | |
| 2019/0022386 A1 | 1/2019 | Gozani | |
| 2019/0046787 A1 | 2/2019 | Tyler et al. | |
| 2019/0201687 A1 | 7/2019 | Ahmed | |
| 2019/0290925 A1 | 9/2019 | Gellman | |
| 2020/0230411 A1 | 7/2020 | McGee et al. | |
| 2020/0297999 A1 | 9/2020 | Pal | |
| 2020/0324147 A1 | 10/2020 | Dai et al. | |
| 2021/0046356 A1 | 2/2021 | Czaja | |
| 2021/0100998 A1 | 4/2021 | Charlesworth | |

OTHER PUBLICATIONS

Tzallas et al., "Perform: A System for Monitoring, Assessment and Management of Patients with Parkinson's Disease", Sensors, 2014, 14, 29 pages.

Wac, "Smartphone as a Personal, Pervasive Health Informatics Services Platform: Literature Review", IMIA Yearbook of Medical Informatics, 2012, 11 pages.

Marshall et al., "Use of a Smartphone for Improved Self-Management of Pulmonary Rehabilitation",Hindawi Publishing Corporation, International Journal of Telemedicine and Applications, vol. 2008, 2007, 5 pages.

International Search Report and Written Opinion for corresponding PCT Application No. PCT/2021/055955 dated Jan. 21, 2022 (32 pages).

International Preliminary Report on Patentability for corresponding international application No. PCT/US2021/055955.

* cited by examiner

SYSTEMS, METHODS AND DEVICES FOR ELECTRICAL STIMULATION THERAPY

CROSS-REFERENCE TO RELATED APPLICATIONS

This application is a continuation of U.S. patent application Ser. No. 17/506,851, filed Oct. 21, 2021, which claims benefit of U.S. Provisional Application No. 63/146,196, filed Feb. 5, 2021, both of which are hereby incorporated by reference in their entireties.

FIELD

The present systems, methods and devices generally relate to the delivery of energy impulses (and/or fields) to bodily tissues for therapeutic purposes. Specifically, these systems, methods and devices relate to the use of non-invasive devices, particularly transcutaneous electrical stimulation devices, for enhancing the body's bone healing process in, for example, spinal fusion patients.

BACKGROUND

The use of electrical stimulation for the treatment of medical conditions has been well known in the art for nearly two thousand years. It has been recognized that electrical stimulation of bone, muscle and/or nerve tissue may promote healing.

Therapeutic stimulator devices have been designed to promote healing after spinal surgery, such as spinal fusion or spondylodesis. Spinal fusion is a neurosurgical or orthopedic surgical technique that joins two or more vertebrae to decompress and stabilize the spine. Spinal fusion may also relieve the pain and pressure from mechanical pain of the vertebra or on the spinal cord that results from pathological conditions of a spinal disc, such as degenerative disc disease, spinal stenosis, spondylolisthesis, spinal fractures, scoliosis and kyphosis. The procedure can be performed at any level in the spine (cervical, thoracic or lumbar) and generally prevents any movement between the fused vertebrae.

After a spinal fusion has been performed, it is necessary for multiple bone fragments to heal together, or "fuse" to create one solid bone. A fusion does not occur immediately at the time of surgery, but rather results from a process called osteogenesis, which is a body's way of growing bony tissue. Over time (e.g., a few months and up to one year), this bone growth process most often unites the bone segments into a solid union of bone.

Unfortunately, in many patients who have undergone spinal fusion, the bones will not grow together and fuse within a normal period of time. This is sometimes referred to as a failed fusion or pseudoarthrosis, and may occur with patients who have had a previously failed fusion, are having a multi-level spinal fusion (i.e., more than one disc in the vertebrae), patients with a diagnosis of Grade III (or worse) spondylolisthesis, or patients with co-morbidities, such as osteoporosis, vascular disease, diabetes, obesity, renal disease, and the like.

Because of these risks, an electrical bone growth stimulator is sometimes used to help enhance the body's bone healing process. Human bone is actually a living tissue and, like skin, has the inherent ability to heal itself when broken or injured. Broken bone helps promote the body's bone healing process by creating its own electrical field. In the same way, application of an electrical stimulator can enhance the body's natural bone healing process.

Electrical bone growth stimulators may be implanted at the time of the spinal fusion surgery in a soft pocket of tissue under the skin in the lower back. In other cases, external bone growth stimulation devices may be worn outside the skin and do not require surgical implantation or extraction. Typically, the external device is worn after spinal fusion either as thin skin pads/electrodes that are placed directly over the fusion site to deliver a type of electrical stimulation called capacitive coupling, or one or two treatment coils placed into a brace or directly onto the skin that deliver a type of electromagnetic field called a Pulsed ElectroMagnetic Field (PEMF) or a Combined Magnetic Field (CMF).

Unlike an internal (implanted) bone growth stimulator, an external bone growth stimulator may also be prescribed for the patient to use several weeks or months after the fusion surgery if the bone is not fusing as desired. Depending on the device and the patient's situation, an external bone growth stimulator will be prescribed to be worn for a specific number of hours each day (typically within the range of 2 hours to 24 hours per day). Sometimes the patient may be allowed to break up the wear time into several one- or two-hour sessions each day, or to vary the times that the device is worn each day, to better suit the patient's schedule. Typically, the external bone growth stimulator will be worn for a period of 3 to 12 months following the surgery.

Current therapeutic stimulator devices provide a demonstrable benefit at improving patient outcomes, provided that patients are compliant in using the device as prescribed or indicated by the treating physician. However, the long treatment period, and the lack of feedback about the course of the therapy, makes this difficult. Consequently, patients' use of therapeutic stimulator devices tends to drop over time. This behavior is due in part to the patients not being able to see progress in their recovery. Most patients perceive satisfaction with their outcome in terms of pain and activity relative to their pre-surgical condition, but find it difficult to track whether such parameters are tracking in a positive direction. As such, most patients evaluate their satisfaction based on current, and/or best and/or worst-case recollections of their status, leading to an outcome as one of: satisfied or dissatisfied. Further, without objective information, many patients feel a constant sense of uncertainty and anxiety about their progress.

Another disadvantage with current external bone stimulation devices is that the device itself can be bulky and uncomfortable. In addition, these devices may limit mobility and/or inhibit the patient from performing certain physical activities. For example, some of these stimulators are attached to a relatively large inflexible frame worn on the back that is attached to a belt that wraps around the patient's waist. The frame and belt are designed to ensure that the electrodes of the stimulator remain in place at the target location external to the fusion site. Unfortunately, the inflexible frame and the belt limit mobility and generally cannot be worn while performing certain physical activities.

Yet another drawback with existing bone stimulation devices is that the user interfaces for controlling these stimulators are unwieldy and difficult to operate. The patient must either remove the simulation device, or bend into an awkward position, to interact with the user interface and operate the device. In addition, current user interfaces often include confusing input controls that do not necessarily correspond with a single output, which makes these devices more difficult to operate and tends to reduce patient compliance with the therapy regimen prescribed by the physician.

Therefore, there exists a need for an external therapeutic stimulator device that provides electrical stimulation to a spinal fusion site, while improving patient compliance in using the device as prescribed by a treating physician. It would be beneficial to provide such an external stimulator with a more elegant user interface, and a device that is comfortable and minimally intrusive to wear so that the patient has normal mobility and can perform normal physical activities while wearing the device. In addition, it would be desirable to provide an external stimulator that determines objective patient information and improves patient feedback, thereby improving patient satisfaction with the device and the overall therapy regimen.

SUMMARY

The following presents a simplified summary in order to provide a basic understanding of some aspects of the present systems, methods and devices. This summary is not an extensive overview of the claimed subject matter. It is intended to neither identify key or critical elements of the claimed subject matter nor delineate the scope of the claimed subject matter. Its sole purpose is to present some concepts of the present systems, methods and devices in a simplified form as a prelude to the more detailed description that is presented later.

Systems, methods and devices are provided for delivering energy impulses (and/or fields) to bodily tissues for therapeutic purposes. The systems, devices and methods are particularly useful for the transcutaneous and non-invasive delivery of electrical impulses to body tissue (e.g., joint, muscle, nerve, bone, ligament, vasculature, and/or other hard or soft tissue, etc.) for enhancing the body's bone healing process in, for example, spinal fusion patients.

In one aspect, a therapeutic stimulator system may comprise a housing for an energy source, a signal generator coupled to the energy source and a timing module coupled to either the energy source or the signal generator. The system may further include one or more electrodes coupled to the signal generator. The signal generator can be configured to generate one or more electrical impulses and to transmit these impulses to the electrode(s). A processor can be coupled to the timing module and includes a computer-readable storage device and/or software application that stores program instructions that allow the processor to determine and store usage levels of the signal generator. In certain embodiments, the program instructions can be configured to determine the usage levels based on a period of time that the one or more electrical impulses are generated by the signal generator and applied to the one or more electrodes. This allows the patient and/or the caregiver to track usage of the stimulator and compare this usage with, for example, a prescribed therapy regimen.

In certain embodiments, the system may further comprise one or more lead wires coupling the electrodes to the housing. The electrodes may have contact surfaces configured for contacting an outer skin surface of the patient, such as a suitable location on the back near the site of a recent spinal fusion. The signal generator may be configured to generate one or more electrical impulses to the one or more electrodes and to transmit those electrical impulses transcutaneously and non-invasively through the outer skin surface to a target location within the spine of the patient. The one or more electrical impulses may be sufficient to enhance bone healing in the patient.

In another aspect, the system may further comprise a user interface configured to receive user status data from the patient. The user interface may be disposed on the housing of the stimulation device or it may be located external to the stimulation device, for example, on an external processing device or a mobile device, such as a Smartphone, tablet, Match, external computer or the like. The user status data may include, for example, the level of pain experienced by the patient, the patient's satisfaction level, his or her mood, recent medication use, particularly pain medication, the patient's perceived aactivity level, the amount of sleep that the patient has received or other data related to the patient's recovery.

The user interface may comprise a plurality of indicators and/or controls, with each indicator or control corresponding with a single output of the stimulation device or a single indication of status. This "one to one" correlation between inputs and outputs makes the device relatively easy to operate and tends to improve patient compliance with the therapy regimen prescribed by the physician.

The system may further include a second processor coupled to the user interface, and a second computer-readable storage device and/or software application that stores program instructions that when executed by the second processor compiles the user status data that has been input by the patient into an aggregate set of data that provides valuable information on the status of the patient. The second processor may be disposed on the stimulation device, the mobile device or an external processing device coupled to the mobile device. Since this information can be inputted by the patient throughout the therapy regimen, it provides historical data for the patient to understand how his/her status has changed throughout the therapy, i.e., pain levels have consistently gone down, medication use has decreased, etc.

In certain embodiments, the second processor may be coupled to the first processor and the system may include a third computer-readable storage device and/or software application that stores program instructions that when executed by the second processor compares the user status data to the usage levels of the device. Alternatively, the third computer-readable storage device may be disposed on the first processor, or a single processor may include all of the computer-readable storage devices. Comparing usage levels of the device directly with the user status data allows the patient to directly correlate usage of the device with his/her status at the time of such usage, e.g., a reduction in pain or a decreased use of medication to alleviate pain may directly correlate with usage. Providing this direct correlation provides confidence to the patient that the therapy regimen is effective, and may improve patient compliance.

The housing may further include an impedance sensor coupled to the one or more electrodes to detect impedance of the electrical impulses transmitted to the target site within the patient. The program instructions may be configured to determine the usage levels based on the impedance. In addition, or in the alternative, the processor may be coupled to the impedance sensor and configured to adjust an amplitude of the one or more electrical impulses based on the impedance. This allows the device to dynamically adjust the amplitude or current applied to the electrodes based on the impedance of, for example, the individual patient, to ensure that a consistent therapeutic signal is delivered to the target site within the patient.

The system may include one or more sensors coupled to the housing or an external processor. The sensors may be configured to detect a physiological parameter of the patient, such as blood flow, blood oxygen, heart rate, heart rate variability, heart rhythm, blood pressure, body temperature, gaze, and gait. The system may further include a computer-readable storage device or software application that stores program instructions to compare the physiological parameters with usage levels of the device or with patient status data.

The system may include a mobile device coupled to the housing. The housing may be attached to the mobile device, or it may be incorporated into the mobile device. Alternatively, the housing may be incorporated into a casing for the mobile device, such as, for example, a casing for a mobile phone. In other embodiments, the mobile device is wirelessly coupled to the housing.

In certain embodiments, the mobile device may include a controller for controlling certain functions of the stimulation device. In this manner, some portions of the control of the stimulation device may reside in controller components that are physically separate from the housing. In this embodiment, separate components of the controller and stimulator housing generally communicate with one another wirelessly. Thus, the use of wireless technology avoids the inconvenience and distance limitations of interconnecting cables. In addition, the stimulator device may be constructed with the minimum number of components needed to generate the electrical impulses, with the remaining components placed in parts of a controller that reside outside the stimulator housing, resulting in a lighter and smaller stimulator housing.

In another aspect, a therapeutic stimulator system may comprise a housing for an energy source and a signal generator coupled to the energy source. The system may further include one or more electrodes coupled to the signal generator and a motion sensor coupled to the housing and configured to sense a motion of the housing. A processor may be coupled to the motion sensor and include a computer-readable storage device and/or software application that stores program instructions that allow the processor to determine a magnitude of motion data obtained from the motion sensor over a plurality of time frames. This allows the patient and/or the prescribing physician to track the patient's motion during use of the stimulator.

In certain embodiments, the computer-readable storage device may store program instructions to determine motion levels indicating a peak vector magnitude of the motion data. The motion sensor may detect the motion data at a frequency of about 5 Hz to about 100 Hz, preferably about 25 Hz, and the processor may be configured to group or parse the motion data into a plurality of bins to create a histogram of the motion data. The system may also include a wireless transmitter within the housing configured to transmit the parsed data associated with the histogram of the motion data to a remote source, such as a mobile device and/or remote processor.

In certain embodiments, the system may further comprise a software application that includes program instructions that, when executed by a processor, converts the parsed data into patient data that may be displayed on, for example, the mobile device or a separate visual display. This converts the parsed data or histogram of the motion data into meaningful information that can be used by the patient or caregiver to monitor patient compliance and/or the effectiveness of the therapy.

Creating a histogram by grouping the motion data into bins allows the system to convert an extremely large data set (i.e., motion data of the housing taken 25 times/second) into manageable data bytes that can be transmitted from the wireless transmitter to a remote processor. This allows the system to effectively transmit the motion data in real-time to provide valuable feedback regarding the patient's motion during treatment.

In an exemplary embodiment, the motion sensor may comprise an accelerometer within the housing that may be configured to measure acceleration of the housing in three perpendicular axes. Since the housing is attached to the patient, this acceleration data is indicative of the patient's movement during treatment.

In some embodiments, the system may determine activity levels of the patient over time. The system can determine the activity levels by sampling the motion data over predetermined time frames (e.g., 1 minute) and calculating a peak vector magnitude of the motion data for the individual time frames. Further, the system can group the samples into a number of predetermined quantity bins (e.g., bin 0 to bin 14), wherein individual bins correspond to respective, different activity levels ranging from a lowest (e.g., no activity) to a highest (e.g., sprinting). The activity data can be used, for example, to create a histogram representing the patient's activity over time. Grouping the activity data into bins converts an extremely large data set (e.g., motion data captured from the user30 times/second for 24 hours) into a much smaller data set that can be transmitted from the wireless transmitter to a remote processor. Doing so can allow system to efficiently transmit the motion data in real-time and to provide valuable feedback regarding the patient's motion during treatment.

In certain embodiments, the system may further comprise one or more lead wires coupling the electrodes to the housing. The electrodes may have contact surfaces configured for contacting an outer skin surface of the patient, such as a suitable location on the back near the site of a spinal fusion. The signal generator may be configured to generate one or more electrical impulses to the one or more electrodes and to transmit those electrical impulses transcutaneously and non-invasively through the outers skin surface to a target location that may be located within the spine of the patient. The one or more electrical impulses may be sufficient to enhance bone healing in the patient.

In another aspect, the system may further comprise a user interface configured to receive user status data from a user of the system. The user interface may, for example, include a mobile device, such as a Smartphone, tablet, Match, external computer or the like. The user status data may include, for example, the level of pain experienced by the patient, the patient's satisfaction level, his or her mood, medication use, particularly pain medication, the patient's perceived aactivity level, the amount of sleep or other data related to the patient's recovery.

The system may further include a second processor coupled to the user interface, and a second computer-readable storage device and/or software application that stores program instructions that when executed by the second processor compiles the user status data into an aggregate set of data that provides valuable information on the status of the patient. Since this information can be inputted by the patient throughout the therapy regimen, it provides historical data for the patient to understand how his/her status has changed throughout the therapy, i.e., pain levels have consistently gone down, medication use has decreased, etc.

In certain embodiments, the second processor may be coupled to the first processor and the system may include a third computer-readable storage device and/or software application that stores program instructions that when executed by the second processor compares the user status data to the motion data. This allows the patient to directly correlate the user status data with the motion data, thereby allowing the patient to track his/her status (e.g., pain levels) with movement during treatment.

In yet another aspect, a portable stimulation device may comprise a housing having an energy source and a signal generator coupled to the energy source. The housing may include an attachment element for removably coupling the housing to a patient and an upper surface directed towards a head of a patient when the attachment element is coupled to the patient. The device may include one or more electrodes coupled to the signal generator and having a contact surface configured for contacting an outer skin surface of a patient. The signal generator may be configured to generate one or more electrical impulses and transmit the one or more electrical impulses to the electrodes and transcutaneously through the outer skin surface to a target area within the patient. The device may further include a user interface coupled to the signal generator and/or the energy source. The user interface may be disposed on the upper surface of the housing so that it is facing the head of the patient. This allows the patient to view the user interface while wearing the device so that he/she can easily monitor status indicators on the device and/or manipulate controls on the user interface to control the device.

In certain embodiments, the attachment element may be configured to attach to a waist of the patient. The attachment element may comprise a clip configured to attach to a belt worn by a patient. The housing is comfortable, ergonomic and minimally intrusive to wear so that the patient has normal mobility and can perform normal physical activities while wearing the device. This increases patient compliance with the therapy regimen.

The user interface may comprise a plurality of indicators and/or controls, with each indicator or control corresponding with a single output of the stimulator device or a single indication of status. This "one to one" correlation between inputs and outputs makes the device relatively easy to operate and tends to improve patient compliance with the therapy regimen prescribed by the physician.

The device may further include a rechargeable battery removably coupled the housing. In certain embodiments, the device will include a separate charging station and a second rechargeable battery. This allows the patient to easily switch out batteries for continuous 24-hour/day use of the device.

In an exemplary embodiment, the rechargeable battery may include a data storage component coupled to the processor within the stimulation device. The processor may be configured to transfer data, such as motion data, usage levels, or any other data collected by the processor, to the data storage component. The data storage component may be accessed by a separate processor external to the stimulation device (e.g., in the mobile device or a separate processing device) when the battery is removed for recharging. This allows large amounts of data to be transferred from the stimulation device to the mobile device, i.e., larger amounts of data that may be possible through wireless transmission alone.

In another aspect, a therapeutic stimulation system may comprise an energy source, a signal generator, a motion sensor, a processor and a computer-readable data storage device storing program instructions. The signal generator may be configured to generate a therapeutic signal and apply the therapeutic signal through a skin of a user to a target stimulation site. The program instructions, when executed by the processor: (1) store a plurality of samples of user motion data generated by the motion sensor, wherein individual samples of the plurality of samples correspond to respective time frames; (2) for individual samples of the plurality of samples of the user motion data, determine respective activity levels from a plurality of predetermined activity levels, wherein individual activity levels of the plurality of predetermined activity levels correspond to different ranges of user activity; (3) parse the plurality of samples into corresponding activity groups of a plurality of predetermined activity groups based on the respective activity levels determined for the individual samples of the plurality of samples; and (4) determine quantities of user activity for individual time periods of a plurality of time periods based on respective quantities of samples of the plurality of samples included in individual activity level groups of the plurality of predetermined activity groups. In some embodiments, the target stimulation site may be in the spine of the user, and the therapeutic signal may be sufficient to enhance bone healing in the user.

The system may further comprise a portable device including the signal generator, the energy source, the processor and the computer-readable data storage device; and a user device including a display device, a second processor and a second computer-readable data storage device, which stores second storing program instructions. The second program instructions, when executed by the second processor, display the quantities of user activity corresponding to the plurality of predetermined time period using the display device. The user motion data may be associated with motion of the wearable portable device. The portable device may include a signal transmitter communicatively connected to the user device.

The program instructions may further control the portable device to generate impedance data based on a flow of current from the signal generator through the skin of the user and determine usage levels of the portable device based on the impedance data. The program instructions may further control the portable device to modify parameters of the therapeutic signal based on the impedance data.

The respective activity level from the plurality of activity levels for the individual samples may comprise peak vector magnitudes of the individual samples or an average vector magnitude of the individual samples. The individual time periods may be about 0.1 to about 10 seconds or about 0.5 to 2 seconds.

The second program instructions, when executed by the second processor, may control the user device to provide a first user interface prompting the user to enter user status information and provide a second user interface receiving the user status information from the user. The user status information may comprise one or more of: level of pain, satisfaction level, mood, medication use, activity level, and amount of sleep.

The stimulation system may further comprise a rechargeable battery detachably coupled to the portable device. The rechargeable battery may comprise an input/output device configured to communicatively connect the portable device to a battery charger and a non-volatile data storage that stores the motion data.

In another aspect, a method for treating a patient comprises generating a therapeutic signal using a signal generator, applying the therapeutic signal through a skin of a user to a target stimulation site and storing a plurality of samples of user motion data generated by a motion sensor is provided. The individual samples of the plurality of samples may correspond to respective time frames. The method may further include: (1) determining, for individual samples of the plurality of samples of the user motion data, respective activity levels from a plurality of predetermined activity levels, wherein the individual activity levels of the plurality of predetermined activity levels correspond to different ranges of user activity; (2) parsing the plurality of samples into corresponding activity groups of a plurality of predetermined activity groups based on the respective activity levels determined for the individual samples of the plurality of samples; and (3) determining quantities of user activity for individual time periods of a plurality of time periods based on respective quantities of samples of the plurality of samples included in individual activity level groups of the plurality of predetermined activity groups. In some embodiments, the step of applying may comprise transmitting the therapeutic signal through the skin to the target stimulation site, wherein the target stimulation site may be located in the spine of the user, and the therapeutic signal may be sufficient to enhance bone healing in the user.

The signal generator and the motion sensor may be housed within a wearable portable device. The user motion data may be associated with motion of the wearable portable device.

The method may further comprise transmitting the quantities of user activity corresponding to the plurality of predetermined time periods from the wearable portable device to a display device and displaying the quantities of user activity corresponding to the plurality of predetermined time periods on the display device.

The respective activity level from the plurality of activity levels for the individual samples may comprise peak vector magnitudes of the individual samples or an average vector magnitude of the individual samples. The individual time periods are about 0.1 to about 10 seconds.

The method may further comprise applying the therapeutic signal from one or more electrodes coupled to the wearable portable device transcutaneously through an outer skin surface of the user to the target stimulation site and generating impedance data based on a flow of current from the signal transmitter through the outer skin surface of the user. Usage levels of the wearable portable device may be determined based on the impedance data. Parameters of the therapeutic signal may be modified based on the impedance data.

The method may further comprise providing a first user interface prompting the user to enter user status information and providing a second user interface receiving the user status information from the user. The user status information comprises one or more of: level of pain, satisfaction level, mood, medication use, activity level, and amount of sleep.

The plurality of samples of the user motion data may be stored in a detachable rechargeable battery that can be removed such that the user motion data is received by a remote processor or display device.

It is to be understood that both the foregoing general description and the following detailed description are exemplary and explanatory only and are not restrictive of the disclosure. Additional features of the present systems, methods and devices will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the present systems, methods and devices, and together with the description serve to explain the principles of the disclosure.

DETAILED DESCRIPTION

Systems, devices and methods are provided for delivering electrical impulses to bodily tissue. The systems, devices and methods are particularly useful for promoting bone healing and controlling pain in for example, spinal fusion patients. In some embodiments, a therapeutic stimulator system enables improved tracking and sharing of treatment and status information. In some embodiments, the therapeutic stimulator system includes a wearable, non-invasive stimulator device and a hub device, such as a smartphone or tablet, that captures stimulator usage data, user motion data and user-provided status data. The captured data can be aggregated to provide feedback to the user and their healthcare provider to improve the user's recovery. The systems and devices also help ensure and demonstrate both compliance with the therapy and higher patient satisfaction through richer and more frequent data sharing between the physician and patient.

The present therapeutic stimulator systems increase efficiency and improve ease of use over conventional systems by reducing power consumption and decreasing quantities of data stored and transferred. For example, in some embodiments, the therapeutic stimulator systems can reduce power drain and provide long battery life (e.g., greater than 24 hours) by manually or periodically pulling data from the stimulator devices, instead of maintaining communication with, for example, a base station that constantly pulls data from the stimulator devices. Additionally, for example, in some embodiments the therapeutic stimulator systems can decrease quantities of information (e.g., accelerometer data)

stored and transferred by the stimulation devices by combining it into a histogram using an algorithm, which parse the information and converts it into a form that is more meaningful to users (e.g., "active hours").

While the following disclosure is presented with respect to electrical stimulation devices for enhancing bone healing in spinal fusion patients, it should be understood that the features of the presently described devices may be readily adapted for use in any type of electrical stimulation device, such as electrotherapy devices, muscle stimulation devices (e.g., transcutaneous electrical nerve stimulation or TENS), nerve stimulation devices, such as sacral nerve stimulators, vagus nerve stimulators, peripheral nerve stimulation (PNS), spinal cord stimulation, tibial nerve stimulators and the like. In addition, while the present disclosure primarily describes non-invasive, transcutaneous nerve stimulation, the features described herein may be readily adapted for other approaches, such as implantable nerve and muscle stimulators and/or percutaneous nerve stimulators.

Figure 1:
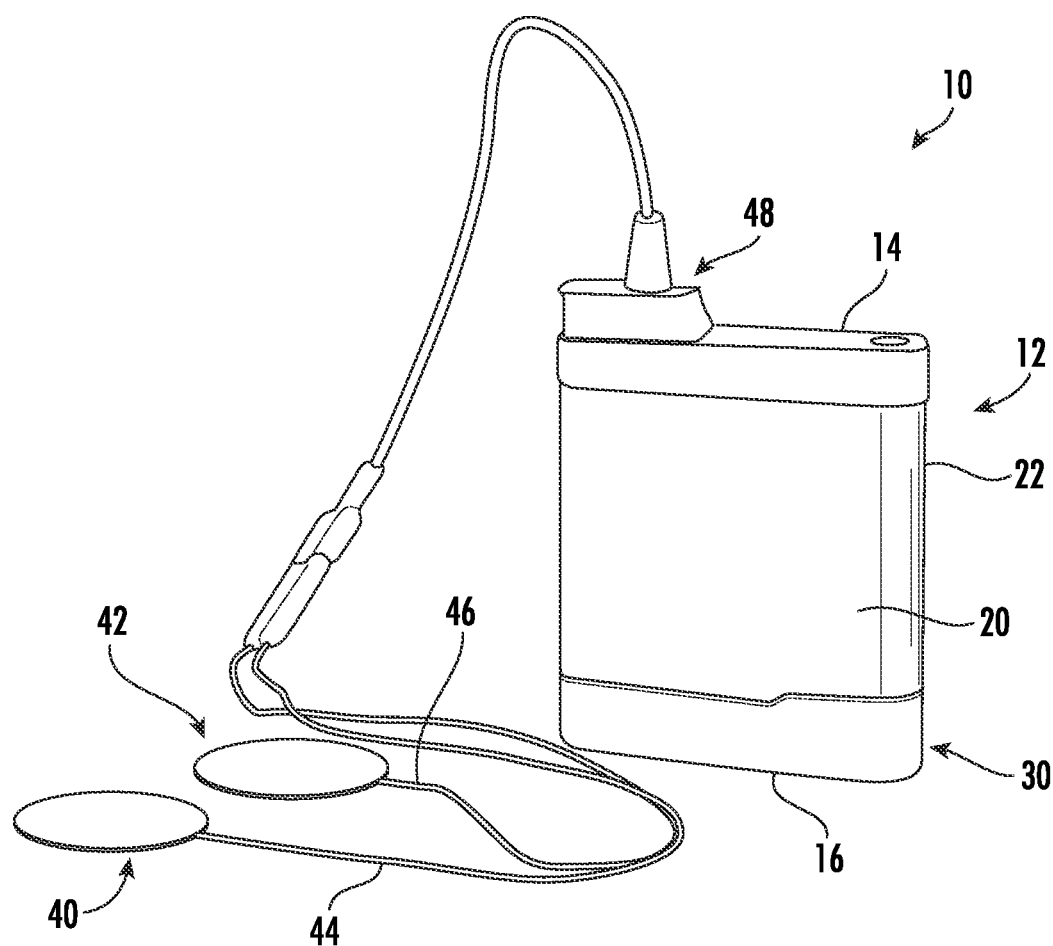
FIG. 1 is a perspective view of a therapeutic stimulation device.

Referring now to FIG. 1, a portable stimulation device 10 will now be described. As shown, stimulation device 10 comprises a housing 12 with upper and lower surfaces 14, 16 and first and second opposing side surfaces 18, 20 connecting upper surface 14 to lower surface 16. In certain embodiments, housing 12 is generally rectangular with side surfaces 18, 20 each having a curved end portion 22, 24 that forms a continuous surface around housing 12 (see also FIG. 2). Side surfaces 18, 20 may be substantially linear, or they may be curved depending on a location housing 12 is worn on a patient's body. For example, inner side surface 12 may have a slightly concave surface while outer side surface 14 may be slightly convex to provide enhanced conformity with a patient's waist.

Housing 12 is preferably lightweight and compact to augment comfort and wearability. Housing 12 may be constructed of any suitable material that provides such functionality, such as metal (e.g., stainless steel or aluminum), plastic (e.g., polycarbonate, polypropylene or polyethylene) or the like. Housing 12 is also relatively thin and ergonomic, preferably having a wall thickness of about 0.05 to 2.0 mm, preferably about 1.0 mm and an enclosure depth of about 15 mm to about 20 mm, preferably about 17.5 mm.

Housing 12 includes an energy source, such as a rechargeable battery (not shown). The rechargeable battery is housed within a battery pack 30 that is removably coupled to lower surface 16 of housing 12. The system may further include a recharging outlet or station (also not shown) configured to receive the rechargeable battery. Alternatively, battery pack 30 may comprise an outlet or other coupling element for directly charging the battery with a suitable electrical connector (i.e., without removing battery pack 30 from housing 12). Providing a rechargeable battery that may be easily switched out allows 24 hour use of the device, which may increase the effectiveness of the device. In other embodiments, the energy source may be located exterior to housing 12 and either directly connected thereto with wires or other electrical connections, or wirelessly coupled to housing 12 via a suitable wireless energy transmitter/receiver device.

In certain embodiments, battery pack 30 includes a data storage component (not shown) coupled to a processor 240 (see FIG. 6) within stimulation device 10. Processor 240 is configured to transfer data, such as motion data, usage levels, or any other data collected by processor 240, to the data storage component. The data storage component may be accessed by a separate processor external to the stimulation device (e.g., in the mobile device 60 or a separate processing device) when the battery is removed for recharging. This allows large amounts of data to be transferred from the stimulation device to the mobile device, i.e., larger amounts of data that may be possible through wireless transmission alone.

Stimulation device 10 further includes first and second electrodes 40, 42 coupled to housing via flexible lead wires 44, 46. Lead wires 44, 46 are preferably at least long enough to extend from housing 12 to the target location on the patient's back (see FIG. 3) when housing 12 is attached to the patient's waist (see FIG. 2). In certain embodiments, lead wires 44, 46 are long enough to allow the patient to attach electrodes 40, 42 to the target location without wearing housing 12 (e.g., by placing it on the bedside table during sleep, carrying housing 12 in a backpack or the like). Lead wires 44, 46 are attached to a connection terminal 48 on upper surface 14 of housing 12, which is coupled to a signal generator 232 within housing 12 (discussed below in reference to FIG. 6). Alternatively, connection terminal 48 may be located on lower surface 16 or opposing side surfaces 18, 20. In yet another embodiment, electrodes 40, 42 may be wirelessly coupled to housing 12 such that lead wires 44, 46 are not required.

Electrodes 40, 42 may comprise any suitable skin pad electrodes configured to contact, and adhere to, an outer skin surface of the patient and to deliver electrical impulses through the outer skin surface to a target location within the patient's body. In one embodiment, electrodes 40, 42 comprise conductive gel pads and have a suitable adhesive layer for bonding electrodes 40, 42 to the patient's skin (see FIG. 3).

Figure 2:
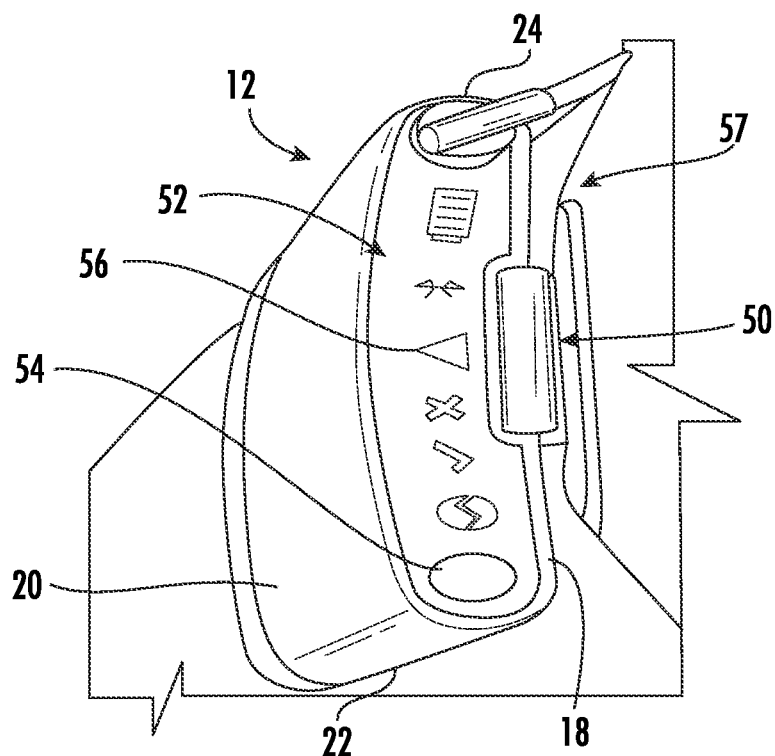
FIG. 2 is a top view of the therapeutic stimulation device of FIG. 1.
Figure 3:
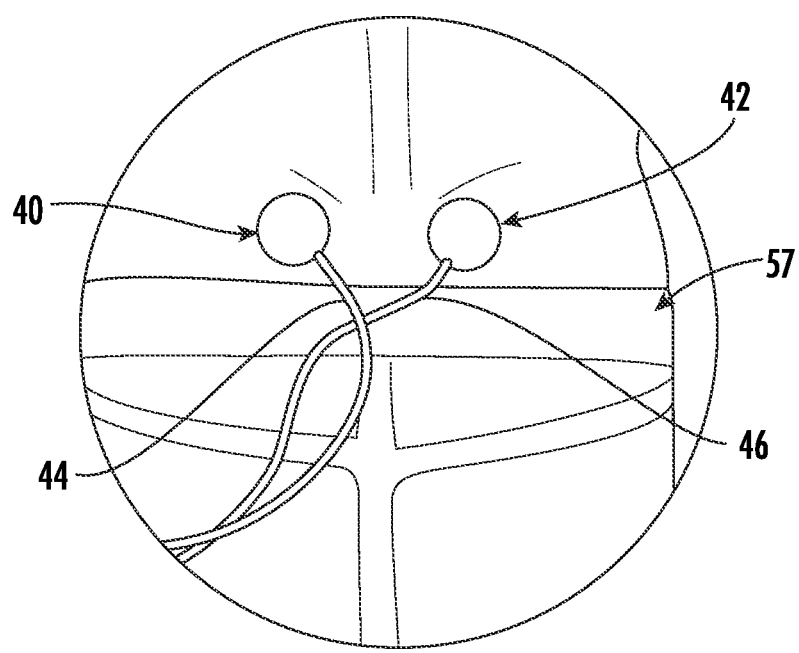
FIG. 3 illustrates first and second electrodes of the stimulation device attached to an outer skin surface of a patient.

Referring now to FIG. 2, housing 12 further includes an attachment element, such as a clip 50, that allows the patient to attach housing 12 to a wearable garment 57, such as a belt, pants, skirt, shorts, or the like. Of course, the attachment element may comprise any suitable releasable coupling element, such as fasteners, snaps, interference fit structures, Velcro and the like. As shown, housing 12 is designed to be worn on the side of the patient's waist to minimize interference with movement, such as walking, kneeling, sitting, bending over or laying down. This ensures that housing is comfortable and non-intrusive to wear, which increases patience compliance with the therapy regimen prescribed by the caregiver.

Of course, it should be recognized that the present disclosure is not limited to an attachment element that couples the housing 12 of device 10 to the patient's waist. For example, device 10 may be configured for attachment to a variety of different wearable garments, such as hats, socks, robes, jackets, pants, shirts, vests, shorts, bibs, coveralls, boots, scarves, ear-muffs, beanies, underwear, wetsuits and the like, and/or to other non-wearable items, such as blankets, sheets, towels, bandages, seats, mattresses, sleeping-bags, and the like.

In one embodiment, significant portions of the control of stimulation device 10 may reside in controller components that are physically separate from the housing 12. For example, the power supply and other electronic components of stimulation device 10 may be located in a separate controller device. In this embodiment, separate components of the controller and stimulator housing generally communicate with one another wirelessly. Thus, the use of wireless technology avoids the inconvenience and distance limitations of interconnecting cables. In addition, the stimulator device 10 may be constructed with the minimum number of components needed to generate the stimulation pulses, with the remaining components placed in parts of a controller that reside outside the stimulator housing, resulting in a lighter and smaller stimulator housing. In fact, the stimulator housing 12 may be made so small that it could be difficult to place user inputs or indicators on the stimulator housing's exterior. Instead, the user interface may be located on a separate control device, such as smartphone touchscreen (discussed below).

In these embodiments, device 10 may be incorporated into a wearable garment. For example, a wearable garment, such as a shirt or pants, may include one or more internal recesses for housing electrodes 40, 42 such that the electrodes can be placed against a target location on the patient's outer skin surface when the patient wears the garment. The wearable garment may include additional features, such as multiple hardpoints, straps or the like, for ensuring that electrodes contact the patient's skin surface and engage this surface sufficiently to transmit the electrical impulses therethrough. The wearable garment may also include a waterproof outer shell around the recesses to insulate the electrodes and associated electronic circuits from moisture, water or other fluids that may contact the garment.

In this embodiment, the electrodes 40, 42 may be coupled to housing 12 through wires, or wirelessly. In either embodiment, the housing may be attached to a different location on the patient (e.g., the waist) or it may be entirely separate from the patient.

Alternatively, stimulation device 10 may be configured for attachment to an accessory device, such as a necklace, watch, earrings, headband or the like. In this latter configuration, device 10 would be much smaller and may, for example, incorporate fewer elements (i.e., electrodes 40, 42, a wireless receiver and associated electronics).

Housing 12 further includes a user interface 52 disposed on upper surface 16 of housing 12. User interface 52 comprises one or more user input controls 54 that allow the user to control device 10, and one or more indicators or icons 56 that provide information to the user about the status of device 10. As shown in FIG. 2, user interface 52 faces towards the patient's head when housing 12 is clipped to the patient's waist. This allows the patient to simply look down and view and/or manipulate user interface 52 without having to remove device 10 from his/her waist or bend into an awkward position to access user interface 52.

Input controls 54 are preferably designed such that a single user input results in only one single output. Similarly, icons 56 are designed such that each indicator corresponds to only one data point, or action required by the user. For example, input controls 54 may include a power control that turns the device On/Off and a signal control that causes the signal generator to transmit electrical impulses to the electrodes. Icons 56 may include a treating indicator, a battery level indicator, a wireless connection indicator, a circuit complete indicator and/or an error/malfunction indicator. Icons 56 may further include a single indicator that alerts the patient that the electrodes are not properly positioned against an outer skin surface such that current may pass therethrough.

In addition to visual indications, device 10 may include an accompanying vibration and/or audible signal or buzzer in case the icons are not visible or when the patient is asleep or otherwise not able to view user interface 52. In this embodiment, input controls 54 may further comprise controls that turn ON/OFF the vibration or the audible signals (e.g., a mute button).

Figure 4:
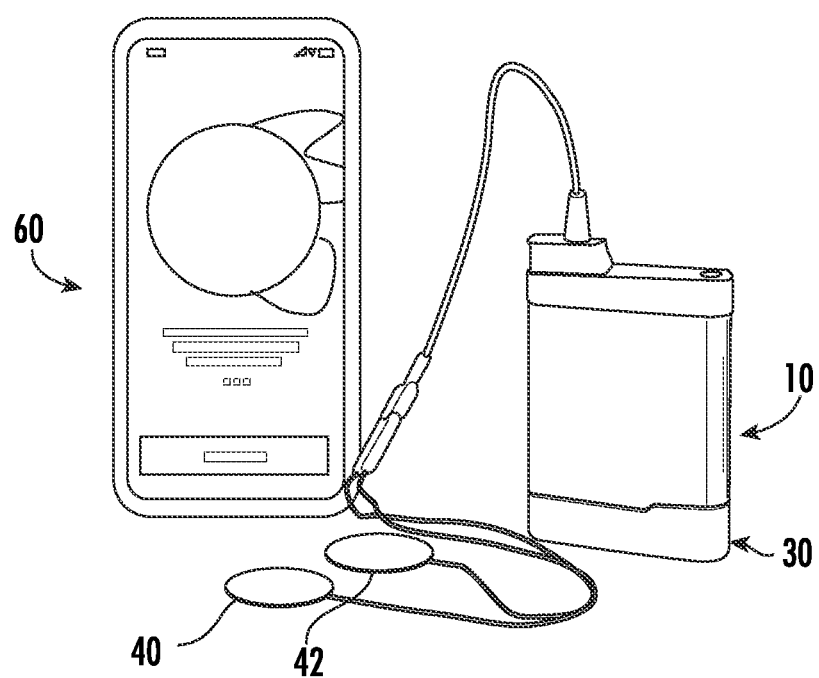
FIG. 4 illustrates the stimulation device of FIG. 1 coupled with a mobile device.

Referring now to FIG. 4, the therapy system may include a mobile device 60 that is wirelessly coupled to stimulation device 10, such as a Smartphone, PDA, tablet PC, palm device, IWatch, laptop computer or the like, Mobile device 60 includes at least a user interface, a user display, a processor and a wireless receiver/transmitter for transmitting data to and from stimulation device 10 and/or to and from other processors (discussed in more detail below). Alternatively, mobile device 60 may also include a direct connector, such as a USB plug, for directly connecting to stimulation device 10. Mobile device 60 may further include a device identifier configured to identify an individual stimulation device 10. The device identifier allows the mobile device 60 to ensure that data transmitted thereto is data from device 10.

In certain embodiments, mobile device 60 includes a suitable user interface and a computer-readable storage device and/or one or more software applications that allow a patient to input current user status information into mobile device 60. The mobile device 60 may include an alert or other alarm that reminds the patient to input user status information on a regular time schedule. The user status information may include, for example, a current level of pain, a satisfaction level, a current mood, an amount of recent medication use (e.g., pain medication), a perceived activity level, the amount of sleep that the patient has recently received or any other data related to the patient's general health or recovery. This user status information is stored within device 60 and may be displayed in a variety of different forms for the user: list form, graphical form, activity reports and the like. The user status information allows the user (and the prescribing physician) to document the user status information, and it may provide historical trends of this information (e.g., have pain levels or medication use gone down over time) to provide a more holistic picture of his/her progress with the therapy regimen.

In certain embodiments, mobile device 60 includes a processor that correlates the user status information with other data received from stimulation device 10, such as motion data and/or usage levels of the device (discussed below). The processor may be configured to allow the display of this correlated information on the mobile device so that the user and/or physician can compare and track the user status information with the motion and usage levels. This provides valuable data to both the user and the physician to help them visualize the effectiveness of the stimulation therapy. In addition, this provides a historical record of this effectiveness so that the patient does not have to remember the user status information at, for example, follow-up visits with the physician. For example, if the patient sees that higher usage levels of the device (and/or usage levels that substantially track the prescribing physician's recommendations) correlate with lower pain levels, higher satisfaction, better moods, etc., the patient will understand that compliance with the therapy regimen (e.g., routine, timing and duration) provides better outcomes. This understanding may provide better patient compliance with the therapy regimen.

Stimulation device 10 may transmit other information to mobile device 60 or directly to a separate processing device (e.g., one operated by a caregiver). This information may include, for example, error data and/or incomplete circuit data produced by stimulation device 10. For example, if the stimulation device 10 produces an incomplete circuit data, this could mean that the patient requires assistance in placement of the electrodes. If the stimulation device 10 produces error data, this could mean that the patient requires assistance troubleshooting device 10.

Mobile device 60 preferably includes one or more software applications that display information that enhances the user experience with stimulation device 10 and enables the patient to track the progress he/she has made with the therapy regimen. In addition, it may provide information on the particular surgical procedure that the patient has undergone, and relevant stage-based content on what the patient may expect during recovery. For example, upon opening the application and creating a profile, the patient may be prompted to provide baseline information on user status, such as mood, pain-level, prescribed medications and the like. The software application may also be configured to prompt the patient to set goals or milestones for his/her recovery, such as pain-free activities. The software application may provide a dashboard or similar display that provides a summary of the data that has been collected during the therapy regimen. This summary data may include, for example, progress towards milestones or goals achieved, progress on recovery, such as pain levels, emotional state and/or activity levels and the like. This information may help the patient avoid recovery setbacks and improve compliance with the therapy.

In certain embodiments, mobile device 60 may include software applications that monitor activity levels of the patient, compare these activity levels to prescribed levels for the individual patient's procedure and/or other data collected from the patient or device 10 (e.g., pain data) and then provide messages to the patient regarding such activity levels (e.g., a warning if the patient is pushing the limits of the prescribed activity levels). The application may also include a list of "approved activities" that are generated by the caregiver that will suit the patient's lifestyle without compromising his/her recovery.

In certain embodiments, the mobile device 60 may be configured to transmit the usage status data, the motion data and/or the usage level data to a separate processor, such as one operated by the caregiver. In these embodiments, the caregiver may also track and record the same correlated information. In certain applications, mobile device 60 may include a patient or user software application and a separate caregiver (e.g., physician) software application. In an exemplary embodiment, the physician software application may be configured to allow the data from individual patients to be aggregated together to form data across a plurality of different patients. This aggregated data may allow the physician to determine the overall effectiveness of the therapy across multiple patients. In addition, it may allow the physician to better understand the impact of usage of the device with the effectiveness of the therapy. For example, the data may show that increased usage of the device and/or improved compliance with the therapy regimen increases overall effectiveness, speed of recovery or reduction in pain.

In certain embodiments, the physician software application may be configured to automatically produce reports of complied data from mobile device 60 and/or stimulation device 10 that may include, for example, patient compliance with the therapy regimen, patient status data (e.g., pain), patient activity information from motion data and/or usage level data. The software application may be designed to aggregate these data into single reports that allow the physician to easily compare, for example, usage level data with pain, patient satisfaction, medication user, activity levels and the like.

Although the device shown in FIG. 4 is an adapted commercially available smartphone, it is understood that in some embodiments, the housing of the stimulator may also be joined to and/or powered by a wireless device that is not a phone (e.g., Wi-Fi enabled device). Alternatively, the stimulator may be coupled to a phone or other Wi-Fi enabled device through a wireless connection for exchanging data at short distances, such as Bluetooth or the like. In this embodiment, the stimulator housing is not attached to the smartphone and, therefore, may comprise a variety of other shapes and sizes that are convenient for the patient to carry in his or her purse, wallet or pocket.

Figure 5:
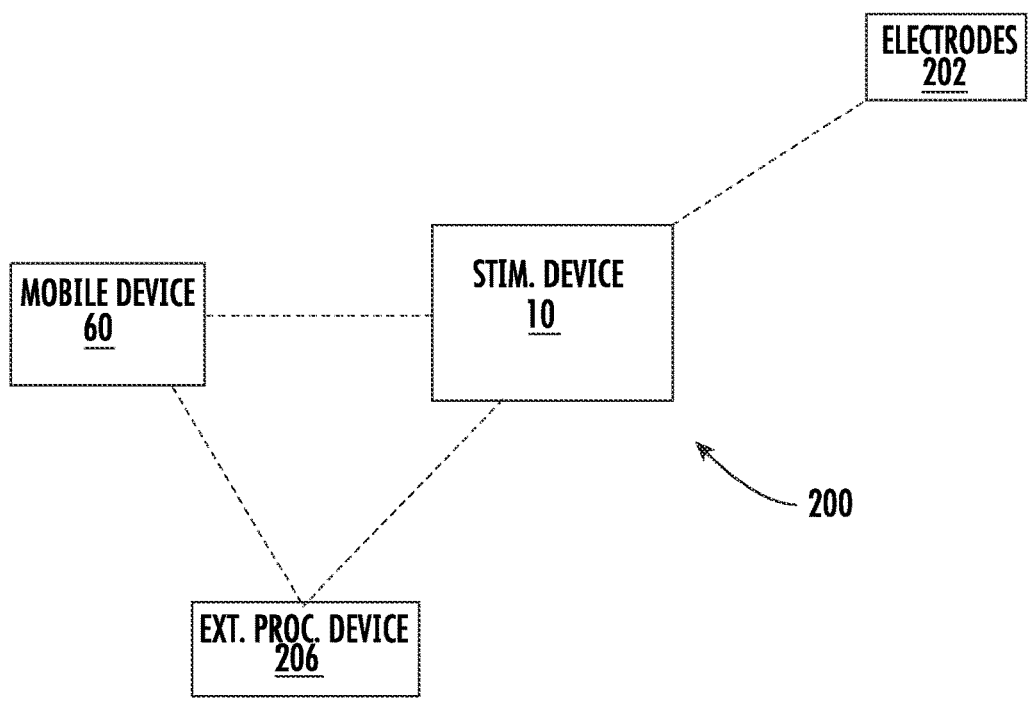
FIG. 5 is a block diagram of a system for delivering electrical impulses to a patient.

Referring now to FIG. 5, a therapy system 200 comprises a stimulation device 10, one or more electrodes 202, a mobile device 60, such as a Smartphone or similar device as discussed above, and an external processing device 206, such as computer, server or other database. Mobile device 60 preferably includes a user interface (not shown) for allowing the patient to input user status data and a wireless receiver/transmitter for receiving data from stimulation device 10 and for transmitting data to external processing device 206. Electrodes 202 may be coupled to stimulation device 10 via leads (as discussed above in reference to FIGS. 1-4) or they may be coupled wirelessly to stimulation device 10. In the latter embodiment, electrodes 202 may also include a wireless receiver for receiving the stimulation signal and suitable electronics for converting the received signal to electrical impulses, as discussed above.

The system 200 may include one or more sensors (not shown) coupled to housing 12, mobile device 60 or an external processor. The sensors may be configured to detect a physiological parameter of the patient, such as body temperature, blood flow, blood oxygen, heart rate, heart rate variability, heart rhythm, blood pressure, gaze and gait. The system may further include a computer-readable storage device that stores program instructions to compare the physiological parameters with usage levels of the device or with patient status data. Suitable sensors for use in the present systems, methods and devices may include PCT and microarray based sensors, optical sensors (e.g., bioluminescence and fluorescence), piezoelectric, potentiometric, amperometric, conductometric, nanosensors or the like.

Figure 6:
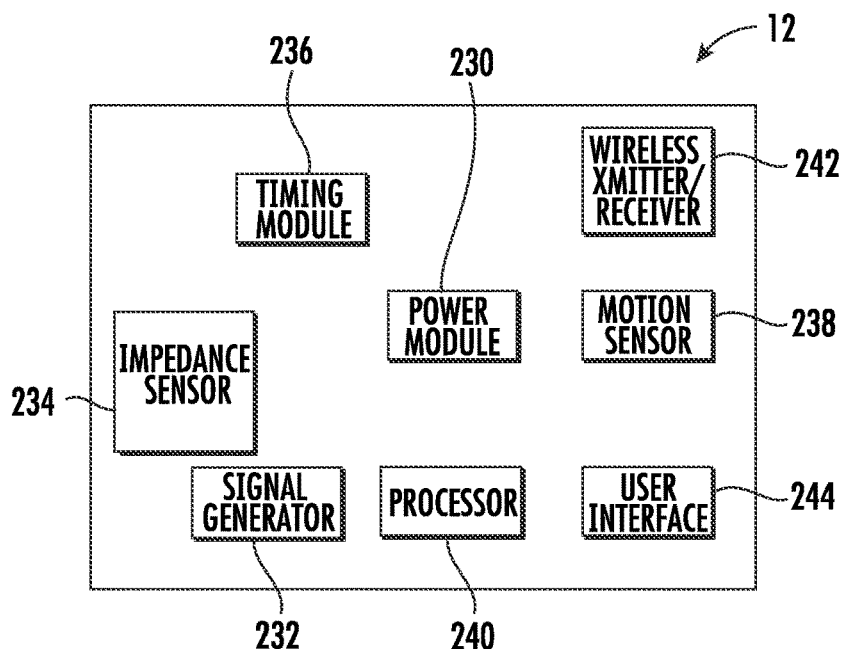
FIG. 6 is a block diagram of the internal components of a stimulation device.

Referring now to FIG. 6, a block diagram of certain internal components of stimulation device 10 will now be described. As shown, stimulator device 10 comprises housing 12 and a power module 230, such as the rechargeable battery described above. Housing 10 further includes a signal generator 232, an impedance sensor 234, a timing module 236 and a motion sensor 238 coupled to a processor 240. Housing 10 may also include a wireless transmitter/receiver 242 and a user interface 244, as discussed above. In certain embodiments, device 10 can comprise a one-way buffer or Firewall between the treatment and communication components of housing 60 to prevent interference/interaction between these two functions of device 10.

Signal generator 232 can generate a therapeutic signal (i.e., electrical impulses) that can be transmitted to electrodes 40, 42. Signal generator 232 may be implemented using power module 236 and a control unit or processor 240 having, for instance, a clock, a memory, etc., to produce a pulse train to the electrodes 40, 42 that deliver a stimulating, blocking and/or modulating impulse to the patient's body. The parameters of the electrical impulses, such as the frequency, amplitude, duty cycle, pulse width, pulse shape, etc., may be programmable by the caregiver. An external communication device may modify the pulse generator programming to improve treatment.

The electrical impulses preferably have a frequency, an amplitude, a duty cycle, a pulse width, a pulse shape, etc. selected to influence the therapeutic result. In an exemplary embodiment, the therapeutic signal comprises a waveform suitable for transcutaneous delivery through an outer skin surface of a patient to a target location (e.g., joint, muscle, nerve, bone, ligament, vasculature, and/or other hard or soft tissue, etc.) within the patient's spine. In this embodiment, the electrical impulses are preferably sufficient to enhance bone healing within the spine, and are particularly suitable for patients recovering from spinal fusion. In an exemplary embodiment, the signal comprises an output waveform of sinusoidal pulses having a frequency of about 50 KHz to about 70 KHz, preferably about 60 KHz. The amplitude of the waveform is preferably in the range of about 5 to about 10 mA (r.m.s.) at impedances between about 100 and 450 Ohms. The amplitude may be greater than about 3 mA (r.m.s.) at impedances between about 450 Ohms and about 750 Ohms.

Impedance sensor 232 is also coupled to electrodes 40, 42 and functions to measure the impedance from current flow between the electrodes 40, 42 and to transmit this impedance to processor 240. Impedance sensor 232 may be located within housing 12 as shown in FIG. 6, or it may be located within connection terminal 48 (FIG. 1), or any other location between electrodes 40, 42 and signal generator 232. Processor 240 includes software program instructions to adjust the amplitude of the current transmitted to electrodes 40, 42 based on this impedance. As discussed further below, this ensures that the amplitude of the electrical impulses transmitted to the target location within the patient will remain substantially within the therapeutic range. Impedance sensor 232 may also be coupled to timing module 236 for measuring usage levels of device 10, as discussed below.

Motion sensor 238 may comprise one or more accelerometers that detect three-axis motion. In certain embodiments, motion sensor 238 can sample outputs of the accelerometers between about five (5) to about one hundred (100) times per second, preferably about twenty-five (25) times per second. Processor 240 may then convert these individual samples into vectors, and the magnitude of the individual vectors are calculated over a time frame (e.g., one second). Processor 240 may then determine the maximum value of the vectors' magnitudes within their respective time frames and may transfer this data to a remote source, such as mobile device 60, via wireless transmitter/receiver 242. Processor 240 may also be configured to group the motion data into a plurality of bins to create a histogram of the motion data. The details of this functionality are discussed in more detail below.

One of the challenges with providing motion data for a therapeutic device that operates over a long period of time is that the motion sensor generates a significant amount of data that would require substantial storage space on the device. Since the device is designed to be wearable, this storage requirement could make the device bulky and more cumbersome for the patient. In addition, the wireless transfer of this large amount of data to a mobile device or other remote processor would take an extensive amount of time. The motion data would either be transferred automatically by the device or manually by the patient through one or more user input controls. In the former case, the automatic transfer of this data would require the device to constantly search for something to wirelessly connect, or pair, with, thereby prematurely draining the battery. In the latter case, the patient would be required to monitor the device during this data transfer, thereby curtailing ease of use and potentially reducing compliance with the therapy regimen.

The present systems and devices provide a solution to these challenges by extracting enough data to provide useful information from the vast amount of data generated by motion sensor 238. This is achieved by parsing the data from the motion sensor 238 into a histogram and then converting this parsed data or histogram into meaningful patient information on a suitable display device. In one embodiment, processor 240 determines a specific parameter set detected by motion sensor 238. This specific parameter set may be, for example, a peak vector magnitude or an average vector magnitude over a specific period of time, e.g., about 0.1 to 10 seconds, preferably about 0.5 to 2 seconds. Processor 240 then stores only the specific parameter set (rather than every data point detected by motion sensor 238) which reduces the overall storage requirements of device 10, and reduces the quantity of data that is transferred from device 10 to, for example, a mobile device or other remote processor.

In certain embodiments, mobile device 60 may include software applications that include goals or milestones for patient activity levels throughout the therapy. The software applications are configured to compare the motion data collected from stimulation device 10 with these goals and to display this comparison on mobile device 60 and/or the caregiver's display. This facilitates compliance with "physician instructed activity" during the patient's recovery.

Timing module 236 may comprise a real-time clock coupled to processor 240 and functions to measure usage levels of device 10, e.g., treatment time, errors (type and when). In some embodiments, timing module 236 tracks the amount of time that signal generator 232 applies electrical impulses to electrodes 40, 42 and transfers this data to processor 240. In other embodiments, timing module 236 can also determine usage information based on impedance measured between electrodes 40, 42. In either of these embodiments, processor 240 is configured to transfer this data to a remote source, such as mobile device 60, via wireless transmitter/receiver 242.

Wireless transmitter/receiver 242 may comprise any suitable device which converts alternating currents to radio waves (or vice versa) for transmitting data to and from stimulation device 10 and mobile device 60. Transmitter/receiver 242 may comprise a radio frequency current generator, one or more antennas and associated firmware. In certain embodiments, device 10 is designed to only transmit information or data from the device 10 to mobile device 60 or another remote source. In these embodiments, element 242 is only a transmitter and device 60 cannot be controlled or otherwise manipulated from an external source.

In certain embodiments, the signal waveform that is to be applied to electrodes 40, 42 of the stimulator device 10 is initially generated exterior to device 10. In these embodiments, stimulator device 10 preferably includes a software application that can be downloaded into the device to receive, from the external control component, a wirelessly transmitted waveform, or to receive a waveform that is transmitted by cable. If the waveforms are transmitted in compressed form, they are preferably compressed in a lossless manner, e.g., making use of FLAC (Free Lossless Audio Codec). Alternatively, the downloaded software application may itself be coded to generate a particular waveform that is to be applied to the electrodes 40, 42. In yet another embodiment, the software application is not downloaded from outside the device, but is instead available internally, for example, within read-only-memory that is present within device 10.

A power amplifier within the housing of the stimulator may then drive the signal onto the electrodes, in a fashion that is analogous to the use of an audio power amplifier to drive loudspeakers. Alternatively, the signal processing and amplification may be implemented in a separate device that can be plugged into sockets on the phone and/or housing of the stimulator to couple the software application and the electrodes.

In addition to passing the stimulation waveform from an external controller to the stimulator housing as described above, the external controller may also pass control signals to the stimulator housing. Thus, the stimulation waveform may generally be regarded as a type of analog, pseudo-audio signal, but if the signal contains a signature series of pulses signifying that a digital control signal is about to be sent, logic circuitry in the stimulator housing may then be set to decode the series of digital pulses that follows the signature series of pulses, analogous to the operation of a modem.

Many of the steps that direct the waveform to the electrodes, including steps that may be controlled by the user via the touchscreen of mobile device 60 are implemented in the above-mentioned software application. By way of example, the software application may be written for a phone that uses the Android operating system. Such applications are typically developed in the Java programming language using the Android Software Development Kit (SDK), in an integrated development environment (IDE), such as Eclipse.

In another embodiment, a base station is provided that that may send/receive data to/from the stimulator, and may send/receive data to/from databases and other components of the system, including those that are accessible via the internet. Typically, the base station will be a laptop computer attached to additional components needed for it to accomplish its function. Thus, prior to any particular stimulation session, the base station may load into the stimulator device 10 parameters of the session, including waveform parameters, or the actual waveform. In one embodiment, the base station is also used to limit the amount of stimulation energy that may be consumed by the patient during the session, by charging the stimulator's rechargable battery with only a specified amount of releasable electrical energy, which is different than setting a parameter to restrict the duration of a stimulation session. This may help to ensure that the temperature of the device remains within acceptable limits for continuous use and wearing of the device. Thus, the base station may comprise a power supply that may be connected to the stimulator's rechargeable battery, and the base station meters the recharge. As a practical matter, the stimulator may therefore use two batteries, one for applying stimulation energy to the electrodes (the charge of which may be limited by the base station) and the other for performing other functions. Alternatively, control components within the stimulator housing may monitor the amount of electrode stimulation energy that has been consumed during a stimulation session and stop the stimulation session when a limit has been reached, irrespective of the time when the limit has been reached.

Figure 7:
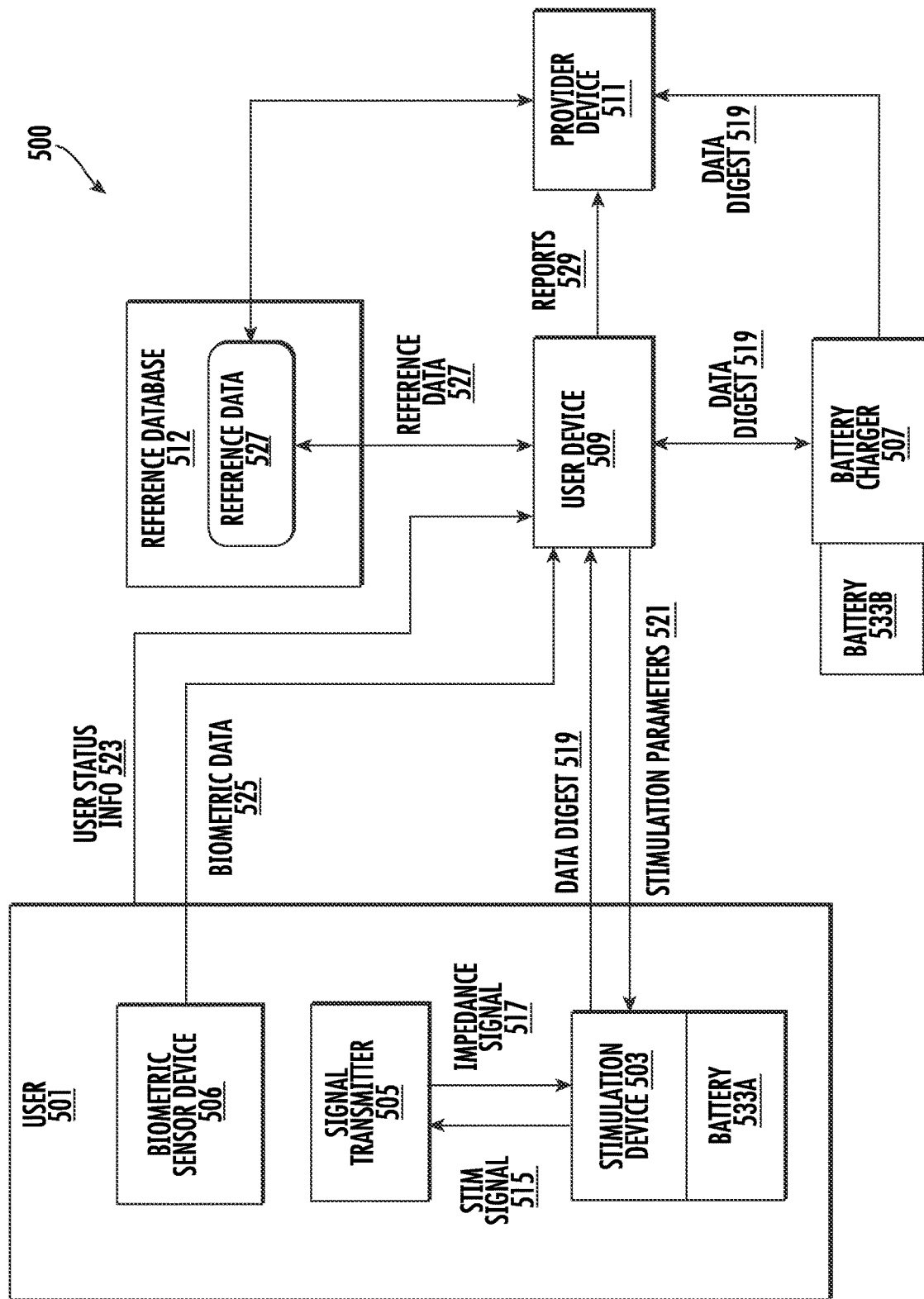
FIG. 7 shows a system block diagram illustrating an example environment for implementing systems and processes.

FIG. 7 shows a block diagram illustrating an example of an environment 500 for implementing the present systems, methods, and computer program products. The environment 500 can include a user 501, a stimulation device 503, a signal transmitter 505, a biometric sensor device 506, a battery charger 507, a user device 509, a provider device 511, and a reference database 512. The stimulation device 503, the signal transmitter 505, and the user device 509 can be the same or similar to those previously described above (e.g., stimulation device 10, electrodes 40, 42, and mobile device 60, respectively).

The user 501 can be any individual. In the non-limiting examples described herein, the user 501 can be a post-surgical patient or an individual with chronic pain. For example, the user 501 can be a patient receiving therapeutic treatment using the stimulation device 503 and the signal transmitter 505 while recovering from spinal fusion surgery. In some embodiments, the user 501 of the stimulation device 503 can periodically provide user status information 523 to the user device 509 throughout the course of the therapeutic treatment. The user status information 523 can include, for example, information indicating the user's level of pain, satisfaction level, mood, medication use, activity level, and amount of sleep, and the like. In some embodiments, the user 501 provides the user status information 523 directly to the user device 509 via a user interface provided by the user device 509.

The stimulation device 503 can generate a stimulation signal 515 and apply it to the user 501 via the signal transmitter 505, as previously described herein. For example, the stimulation device 503 can be a level 1 clinical device and the stimulation signal 515 can be a therapeutic electric signal. In some embodiments, the stimulation signal 515 comprises a waveform for transcutaneous delivery through an outer skin surface of a patient to a target location within the user's spine. The stimulation signal 515 can have a frequency, an amplitude, a duty cycle, a pulse width, a pulse shape, etc. selected to provide a therapeutic benefit. For example, the stimulation signal 515 can be a waveform of substantially sinusoidal pulses having a frequency of about 50 kHz to about 70 kHz, about 60 kHz. The amplitude of the waveform can be in the range of about 5 to about 10 mA (r.m.s.) at impedances between about 100 and about 450 Ohms. The amplitude may be greater than about 3 mA (r.m.s.) at impedances between about 450 Ohms and about 750 Ohms.

In some embodiments, the stimulation device 503 provides a user-interface (e.g., user interface 52) that controls operation of the stimulation device 503, including controlling and modifying the stimulation signal 515. In some embodiments, the user interface allows the user 501 to select one or more parameters or combinations of parameters for the stimulation signal 515. For example, the user 501 can select one of a number of preprogramed profiles for the stimulation signal 515 having different amplitudes and pulse widths.

The stimulation device 503 can generate a data digest 519. In some embodiments, the data digest 519 can be a data structure that logs activity of the user 501 and the user's use of the stimulation device 503 in a time-ordered sequence. For example, the data digest 519 can be a time-indexed data structure that stores data samples from various sources in time-wise association with one another. In some embodiments the data digest 519 includes information indicating usage periods of the stimulation device 503, motion levels of user 501, and errors detected by the stimulation device 503. For example, the stimulation device 503 can generate the data digest 519 based on an impedance signal 517 received from the signal transmitter 505 and motion data generated by motion sensors in the stimulation device 503.

The biometric sensor device 506 can be a wearable device including one or more sensors that generate biometric data 525 indicating physiological parameters of the user 501 and provide the biometric data 525 to the user device 509. The biometric sensor device 506 can be, for example, a smartwatch, waistband, instrumented shoes, instrumented headgear, or the like. The biometric sensor device 506 can include one or more of "PCT" sensors, microarray sensors, optical sensors (e.g., bioluminescence and fluorescence), microelectromechanical sensors, piezoelectric sensors, potentiometric sensors, amperometric sensors, conductometric sensors, nanosensors, or other suitable sensors. The physiological parameters detected by the sensors can include or more of body temperature, blood flow, heart rate, heart rate variation, heart rhythm, blood pressure, blood oxygen, gaze, and gait.

The signal transmitter 505 can be one or more devices that receives the therapeutic stimulation signal 515 from the stimulation device 503 and applies the stimulation signal 515 to the user 501. As previously described, the signal transmitter 505 can include a receiver for receiving the stimulation signal 515 and for converting it to electrical impulses. In some embodiments, the signal transmitter 505 comprises two or more electrodes (e.g., electrodes 40, 42) that adhere to skin of the user 501 and provide the stimulation signal 515 to a surgical site through direct contact with skin of the user 501. In some other embodiments, the signal transmitter 505 is incorporated into a wearable unit (e.g., wearable garment 57) that retains the electrodes in contact with the skin of the user 501.

The battery charger 507 can be a device configured to connect with one or more batteries 533A, 533B of the stimulation device 503 and provide power to the batteries 533A, 533B. For example, a housing of the battery charger 507 can have an interior volume corresponding to the shape of the outer housing of the batteries 533A, 533B. The battery charger 507 can include a power supply and control electronics that manage recharging of the batteries 533A, 533B. Additionally, in some embodiments, the battery charger 507 includes communication electronics that receive the data digest 519 stored in the batteries 533A, 533B by the stimulation device 503, and can share the data digest 519 with other devices, such as the user device 509 and the provider device 511 while one of the batteries 533A, 533B is not in use. For example, in response to detecting insertion of the battery 533B, the battery charger 507 can provide the data digest 519 to the provider device 511 via a wireless connection to the Internet. In some embodiments, the battery charger 507 can store the data digest 519, and periodically provide it to the user device 509 and the provider device 511 (e.g., once per day). In some other embodiments, the battery charger 507 provides the data digest 519 once per charging session, such as in response to the battery 533B being connected to the battery charger 507. As a practical matter, the stimulation device 503 can use two batteries 533A and 533B, wherein the battery 533A powers the signal transmitter 505 and store the data digest 519. Meanwhile, the battery charger 507 recharges the second battery 533B while communicating information previously recorded in the data digest 519.

The user device 509 can be a computing device that communicates with the user 501, the stimulation device 503, the biometric device 506, the battery charger 507, and the reference database 512 via one or more wired or wireless data communication channels. In some embodiments, the user device 509 is a portable computing device, which can be the same or similar to that previously described herein (e.g., user device 60). In some other embodiments, the user device 509 is a desktop computer or a laptop computer. In some other embodiments, the user device 509 is a communication node that relays information from the user 501, the stimulation device 503, the biometric sensor device 506, and the reference database 512 through a network (e.g., the Internet) to a remote computing system, such as the provider device 511.

The user device 509 can receive information, including the data digest 519 from the stimulation device 503, user status information 523 from the user 501, biometric data 525 from the biometric sensor device 506, and reference data 527 from the reference database 512. In some other embodiments, the user device 509 receives the data digest 519 from the batteries 533A, 533B during recharging in the battery charger 507. The user device 509 can log information in association with timestamps indicating a time the information was generated or received. For example, the information received from the user 501, the stimulation device 503, the biometric sensor device 506, and the reference database 512 can be stored in time-wise association with one another based on their respective timestamps.

Additionally, the user device 509 can store and process the data digest 519, the user status information 523, and the biometric data 525 to determine correlations and trends. Further, the user device 509 can use this information to generate reports 529 providing feedback to the user 501 and the provider device 511. In some embodiments, the reports 529 indicate the user's activity, daily treatment schedule compliance, and historical performance. For example, the reports 529 can aggregate time-indexed data indicating the user's usage, activity, and user status (e.g., pain, discomfort, and mood) over a period of time (e.g., daily, monthly, quarterly, and annually).

Further, in some embodiments, the user device 509 provides user interfaces for configuring and controlling the stimulation device 503, for receiving information from the user 501 (e.g., user status information 523 and biometric data 525), and providing information to the user (e.g., reports 529). Configuring and controlling the stimulation device 503 can include receiving selections of stimulation parameters 521, such as waveform parameters, or an actual waveform. In some embodiments, the stimulation parameters 521 can limit energy consumed during a therapeutic session to a predetermined maximum amount of total power, which is different than setting a parameter to restrict the duration of a stimulation session to prevent a temperature of the stimulation device 503 from exceeding a predetermined limit for continuous use and wearing of the device. The user interface can also interact with the user 501 periodically elicit and receive the user status information 523 form the user 501. The user interface can also interact with the user 501 to configure and display various reports 529, such as usage reports, activity reports, user status reports, and the like. In some embodiments, the user interface combines information included in the reports 529 with other information, such as user-specific goal and target information stored on the user device 509 or at the reference database 512.

The provider device 511 can be one or more computing devices that receive the reports 529 from one or more user devices 509 of one or more users 501. In some embodiments, the provider device 511 can be a server or a personal computer. Additionally, in some embodiments, the provider device 511 can also receive anonymized user data aggregated from a number of different user devices other than the user device 509 used by users other than the user 501. In some embodiments, the provider device 511 is a computing device of a healthcare provider that is authorized to view the user's data.

The reference database 512 can be one or more storage systems storing reference data 527 and communicatively linked to the user device 509 and the provider device 511. In some embodiments, the reference database 512 is a network storage system remote from the user device 509 and the provider device 511. In some other embodiments, the reference database 512 is stored locally by the user device 509 or provider device 511. The reference data 527 can include, for example, user data, provider data, and device data. The user data can include, for example, registration data, profile data, prescription information, medical history data, and scheduling information. The user data can also include therapeutic plans, goals, targets, timelines, and milestones. The provider data can include, for example, provider profile data, scheduling information, and medication prescription information. The device data can include, for example, device profile and setting information for the stimulation device 503.

Figure 8:
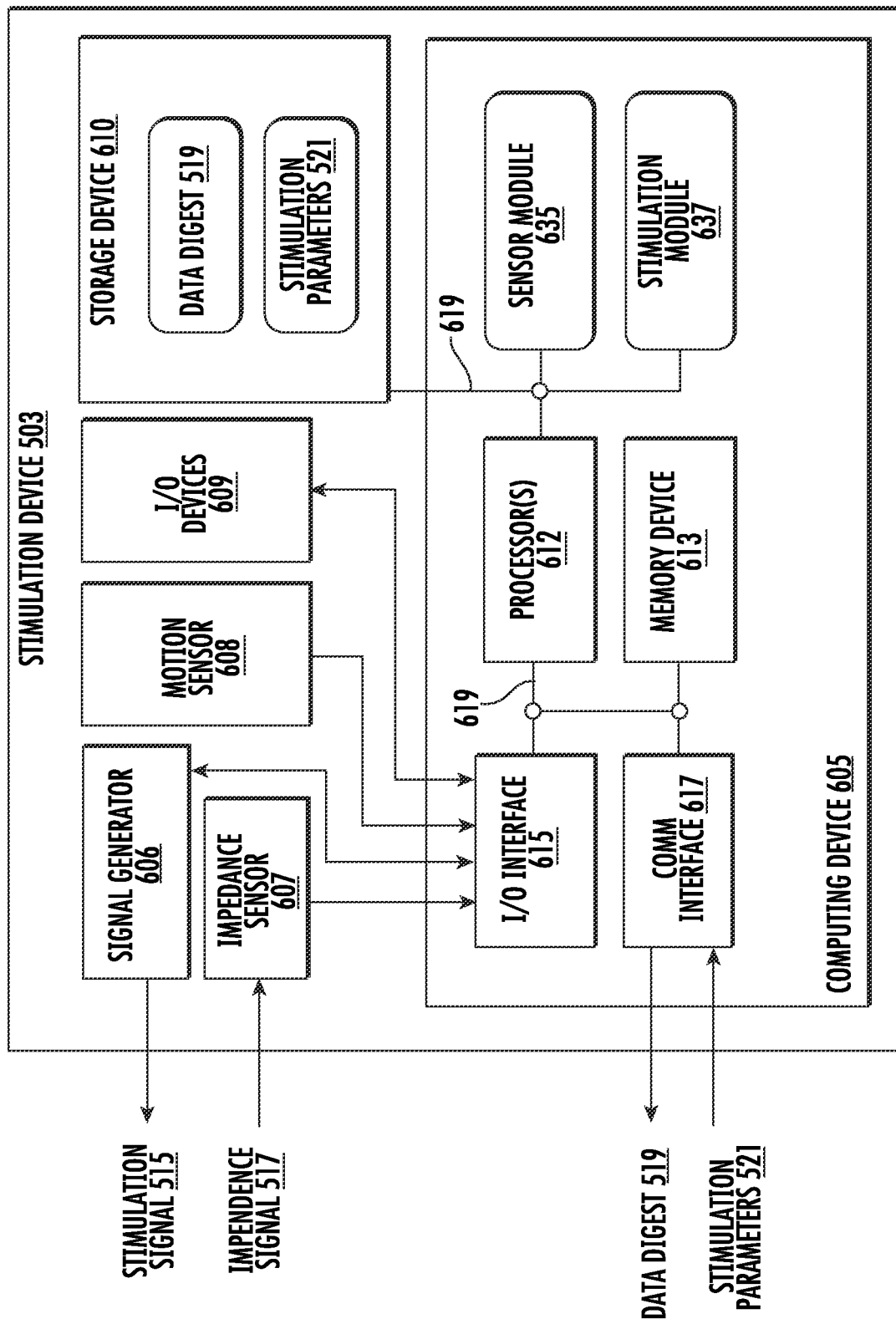
FIG. 8 shows a system block diagram illustrating an example of a stimulation device.

FIG. 8 shows a system block diagram illustrating an example of a stimulation device 503. The stimulation device 503 includes hardware and software that perform processes and functions described herein. In some embodiments, the stimulation device 503 includes a computing device 605, a signal generator 606, an impedance sensor 607, a motion sensor 608, I/O devices 609, and a storage system 610.

In some embodiments, the computing device 605 can include one or more processors 612 (e.g., microprocessor, microchip, or application-specific integrated circuit), one or more memory devices 613 (e.g., random-access memory and/or read-only memory), and I/O interface 615, and a communication interface 617. In some embodiments, the processor 612 includes a real-time clock that produces one or more clock signals that can be used to timestamp data. The memory devices 613 can include a local memory (e.g., a random-access memory and a cache memory) employed during execution of program instructions. Additionally, the computing device 605 can include at least one communication channel 619 (e.g., a data bus) by which it communicates with the storage system 610, the memory device 613, the I/O interface 615, and the communication interface 617.

It is understood that the computing device 605 can comprise any general-purpose computing article of manufacture capable of executing computer program instructions installed thereon. However, the computing device 605 is only representative of various possible computing devices that can perform the processes described herein. To this extent, in embodiments, the functionality provided by the computing device 605 can be any combination of general and/or specific purpose hardware and/or computer program instructions. In each embodiment, the program instructions and hardware can be created using standard programming and engineering techniques.

The signal generator 606 can be a device that generates the stimulation signal 515. The signal generator 606 can, for example, produce one or more selectable signal pulse trains. In some embodiments, a user (e.g., user 501) can select one or more parameters (e.g., stimulation parameters 521) of the stimulation signal 515, such as frequency, amplitude, duty cycle, pulse width, pulse shape, via the I/O devices 609. Additionally or alternatively, in some embodiments, an external device (e.g., provider device 511 or reference database 512) can provide the stimulation parameters 521 or other control information to the stimulation device 503.

The impedance sensor 607 can be one or more devices that measure impedance from current flow of a signal transmitter (e.g., signal transmitter 505), such as between electrodes (e.g., electrodes 40, 42) and generates an impedance signal 517 indicating the magnitude of the impedance. In some embodiments, the impedance signal 517 is a logical signal (e.g., having either a low or a high state) indicating whether or not the signal transmitter is conducting current through the user's skin.

The motion sensor 608 can be one or more devices that generate motion data by detecting movement of the stimulation device 503. In some embodiments, the motion sensor 608 can include one or more accelerometers. For example, the motion sensor 608 can be a three-axis accelerometer. The motion data can be a representing magnitude of the accelerations along one or more of the axes, or a combination thereof. For example, values included in the signal or data stream output by the motion sensor 608 can indicate a total magnitude of the accelerations along the three axes. The magnitude of the signal or a data stream can correspond to different levels of user activity, for example, sleeping, sitting, walking, jogging, sprinting, or any other activity.

The I/O devices 609 can include one or more devices that enable the user to interact with the stimulation device 503 (e.g., a user interface) and/or any device that enables the stimulation device 503 to communicate with one or more other computing devices using any type of communication link. The I/O devices 609 can include, for example, a touchscreen display, a keypad, one or more selectors, one or more indicators. The I/O device 609 can provide a user interface, as previously described herein and additionally described below.

The storage device 610 can store data received and generated by the stimulation device 503, including a data digest 519 and stimulation parameters 521. The data digest 519 can store a time-indexed log of data obtained from the motion sensors 608 and impedance data obtained from the impedance signal 517.

The I/O interface 615 can control data flow between the processor 612 and the signal generator 606, the impedance sensor 607, the motion sensor 608, and the I/O devices 609. For example, the I/O interface 615 can communicate selected stimulation parameters 521 from the processor 612 to the signal generator 606. The I/O interface 615 can also communicate impendence information from the impedance sensor 607 to the processor 612. Further, the I/O interface 615 can communicate motion information from the motion sensor 608 to the processor 612. Moreover, the I/O interface 615 can communicate user inputs and indications transmitted between the I/O devices 609 and the processor 612.

The communication interface 617 can include any device interconnecting the computing device 605 with an information network (e.g., a local area network, a wide area network, and the Internet) enabling the stimulation device 503 to communicate with other computing systems and information storage systems (e.g., user device 509). In some embodiments, the communication interface 617 uses communication protocols that establish secure communication links satisfying HIPPA requirements.

The processor 612 executes computer program instructions (e.g., an operating system and/or application programs), which can be stored in the memory device 613 and/or the storage device 610. In some embodiments, the processor 612 can also execute computer program instructions for a sensor module 635 and a stimulation module 637. The sensor module 635 can be software, hardware, or a combination thereof that processes the information provided by the impedance sensor 607 and the motion sensor 608 (e.g., via the I/O interface 615). In some embodiments, the sensor module 635 samples the impedance information and the motion information at a predetermined rate. Additionally, the sensor module 635 can timestamp the samples of the impedance information and the motion information using a real-time clock. Further, the sensor module 635 can condition the samples of the impedance information and the motion information to, for example, amplify, normalize, de-jitter, and de-noise the information. For example, the sensor module 635 can sample the impedance information and the motion information respectively output by the impedance sensor 607 and the motion sensor 608 at a rate of about 30 Hertz, determine values of the output within one of 15 predefined ranges, and record the values along with timestamps in the data digest 519.

The stimulation module 637 can be software, hardware, or a combination thereof that controls the signal generator 606 to generate the stimulation signal 515 based on stimulation parameters 521. As noted above the stimulation parameters 521 of the stimulation signal 515 can include frequency, an amplitude, a duty cycle, a pulse width, and a pulse shape. In some embodiments, the stimulation parameters 521 can be predetermined values stored in the storage device 610. In some other embodiments, the stimulation parameters 521 can be dynamically updated and provided from an external device (e.g., user device 509, provider device 511, or reference data 527). In some embodiments, the stimulation module 637 adjusts the amplitude of the stimulation parameters 521 based on the impedance data output by the sensor module 635 based on the impedance signal 517. By doing so, the amplitude of the stimulation parameters 521 transmitted to the user can remain substantially within a desired therapeutic range. It is understood that, in some embodiments, the signal waveform can be generated externally from the stimulation device 503. In such embodiments, the stimulation device 10 can include a software application that can be downloaded into the device to receive, from the external control component, a wirelessly transmitted waveform, or to receive a waveform that is transmitted by cable. If the waveforms are transmitted in compressed form, they can be compressed in a lossless manner, e.g., making use of FLAC (Free Lossless Audio Codec). Alternatively, the downloaded software application may itself be coded to generate a particular waveform that is to be output by the signal generator 606.

Figure 9:
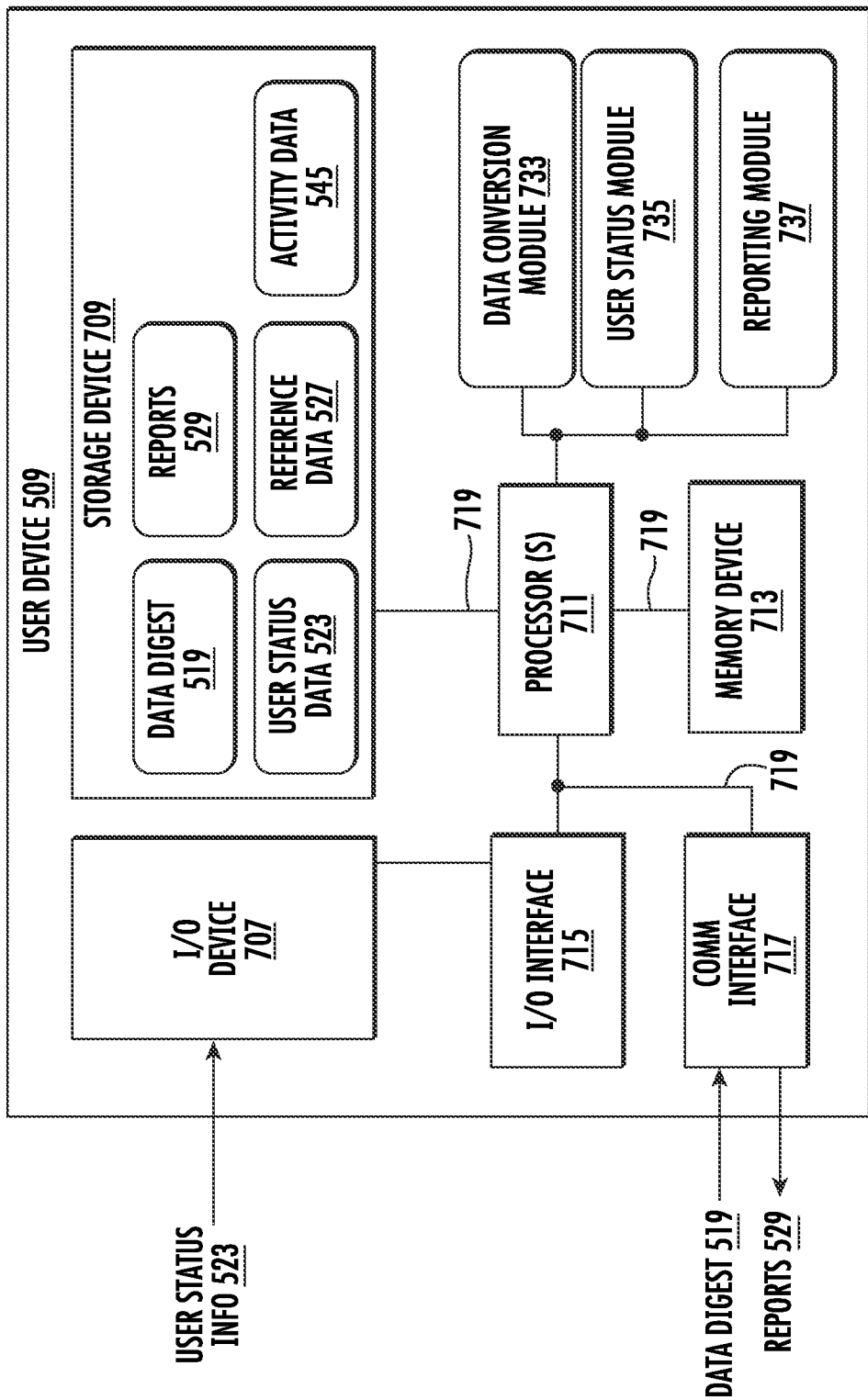
FIG. 9 shows a system block diagram illustrating an example of a user device.

FIG. 9 shows a system block diagram illustrating an example of a user device 509, which can be the same or similar to that described above. The user device 509 includes hardware and software that perform processes and functions described herein. In some embodiments, the user device 509 includes one or more input/output (I/O) devices 707, storage system 709, one or more processors 711, one or more memory devices 713, an I/O interface 715, a communication interface 717, and a data bus 719, all of which can be the same or similar to those previously described above. The processor 711 executes computer program instructions (e.g., an operating system and/or application programs), which can be stored in the memory device 713 and/or the storage system 709. The processor 711 can also execute computer program instructions for a data conversion module 733, a user status module 735, and a reporting module 737.

The data conversion module 733 can be software, hardware, or a combination thereof that processes motion and usage information in the data digest 519 to determine the activity data 545 and store it in the storage device 709. Determining the activity data can include sampling the motion and usage information in consecutive time frames (e.g., one second), determining a peak value of the information in the individual time frames, and classifying the samples as one of a predetermined number (e.g., 15) of activity levels based on their respective peak values. Determining the activity data can also include grouping the samples from a predetermined time period (e.g., an hour) together based on their respective activity levels.

Figure 15A:
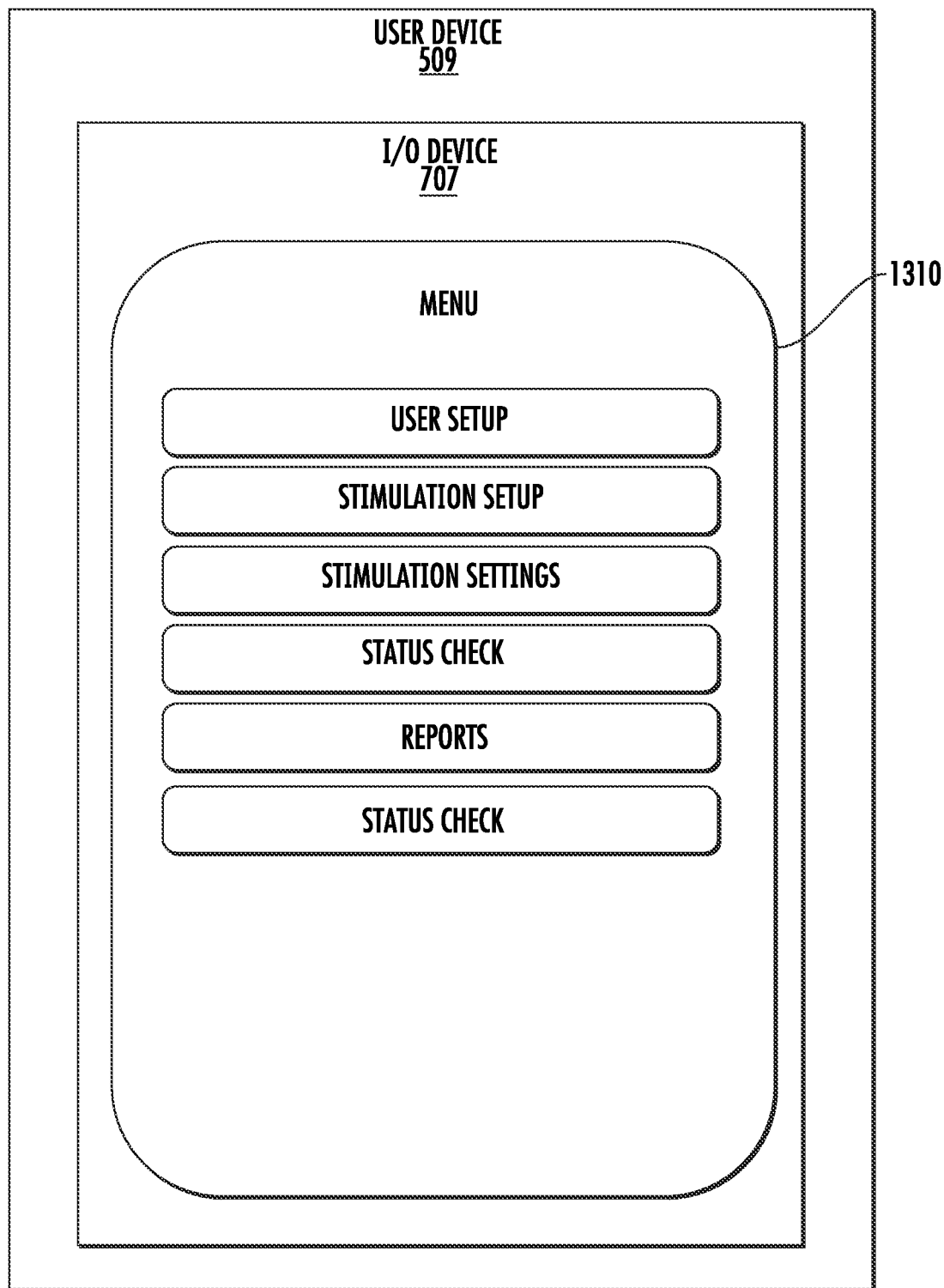
FIGS. 15A, 15B, 15C, 15D, 15E, 15F, and 15G show images illustrating exemplary screenshots of a user-interface provided by a user device.
Figure 15B:
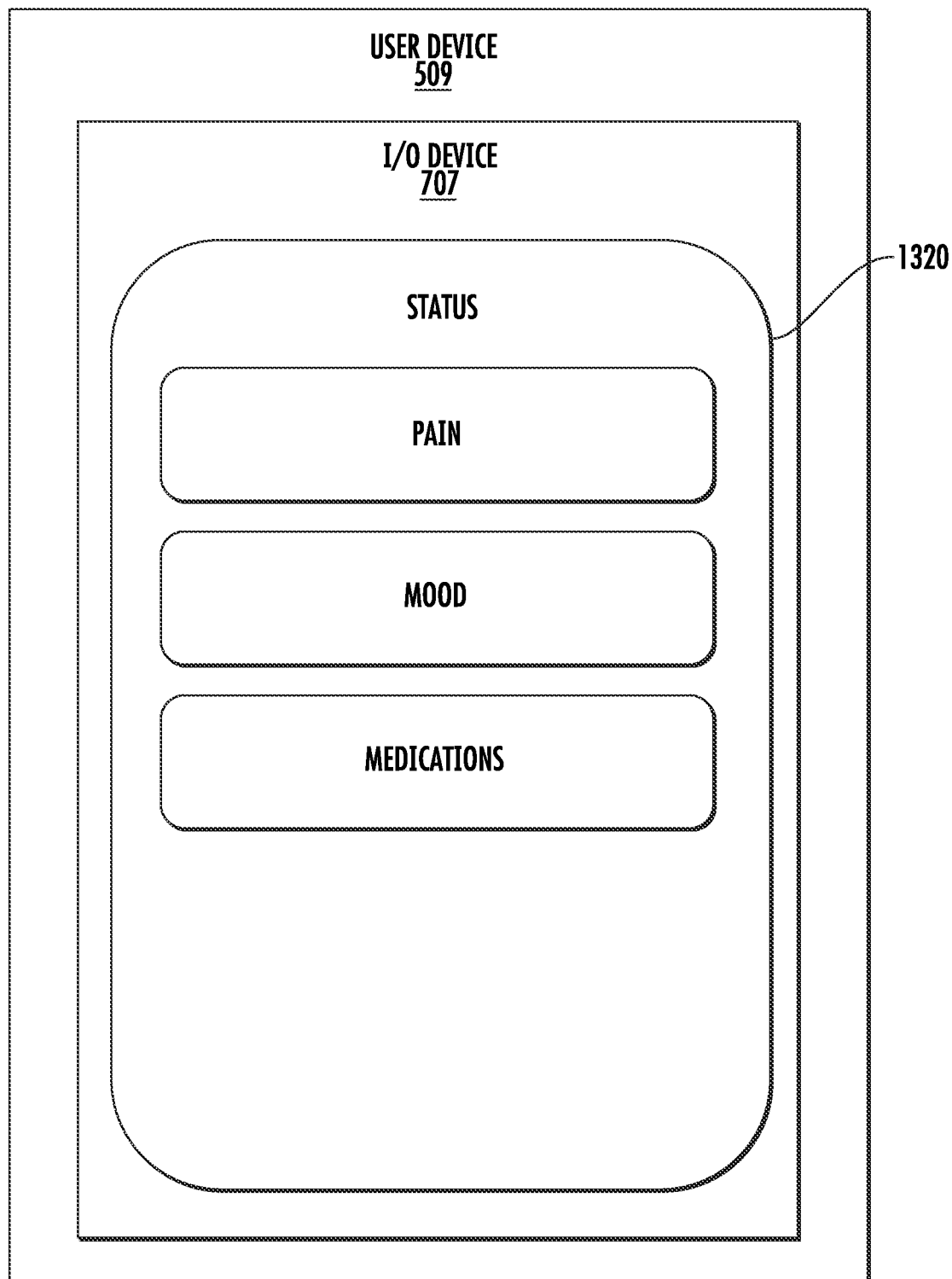
Figure 15C:
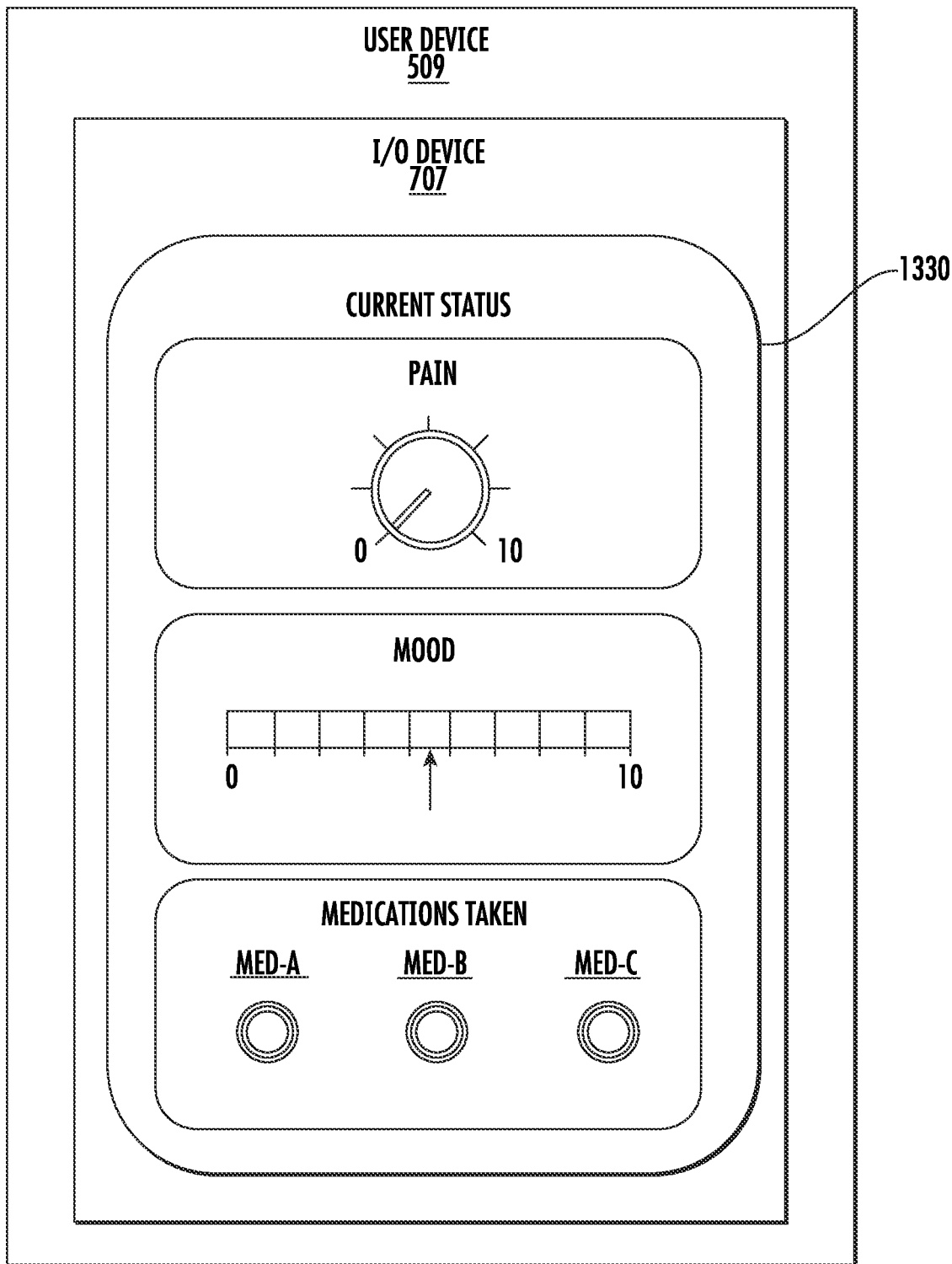
Figure 15D:
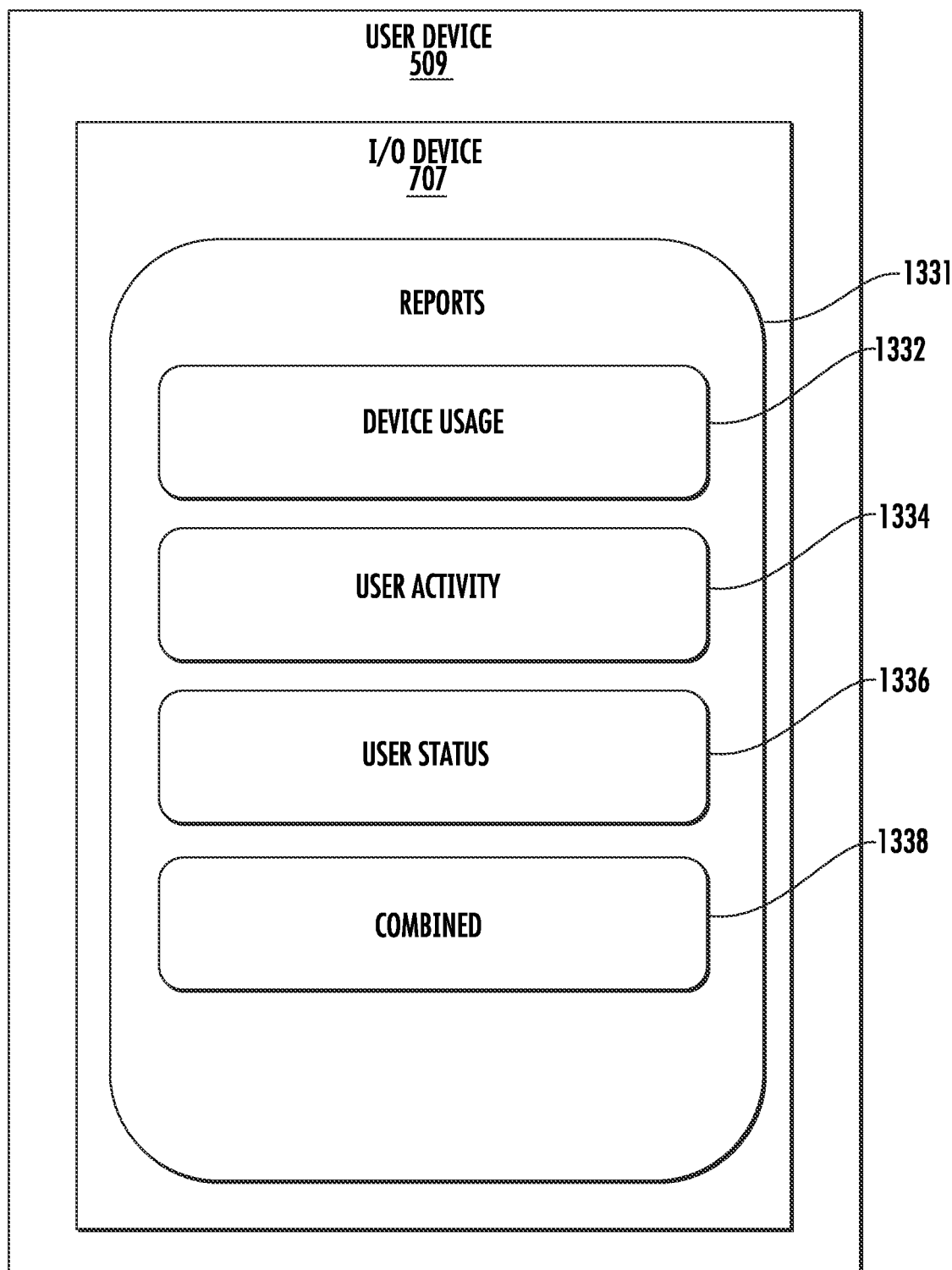

The user status module 735 can be software, hardware, or a combination thereof that elicits and receive the user status information 523 from a user and records it in the storage device 709. In some embodiments, the user status module 735 elicits the user status information 523 by periodically and automatically displaying prompts to the user via the I/O device 707. For example, the I/O device 707 can be a touchscreen graphic user interface of a smartphone. The user status module 735 can periodically (e.g., hourly) display interactive pop-up messages prompting the user to enter user status information 523, such as illustrated in FIG. 15B. Further, the user status module 735 can display an interactive data entry form using the I/O device 707 prompting the user to enter information regarding, for example, their level of pain, their satisfaction level, their mood, their recent medication use, their activity level, their amount and quality of sleep, and other such related their current condition, The user status module 735 can periodically (e.g., hourly) display interactive pop-up messages prompting the user to enter the user status information 523, such as illustrated in FIG. 15C. In some embodiments, the prompts may include questions and information tailored to the user based on, for example, user-specific and provider-specific information, such as prescription regimens, treatment plans, goals, milestones, and the like, which can be stored in the reference data 527.

Figure 15E:
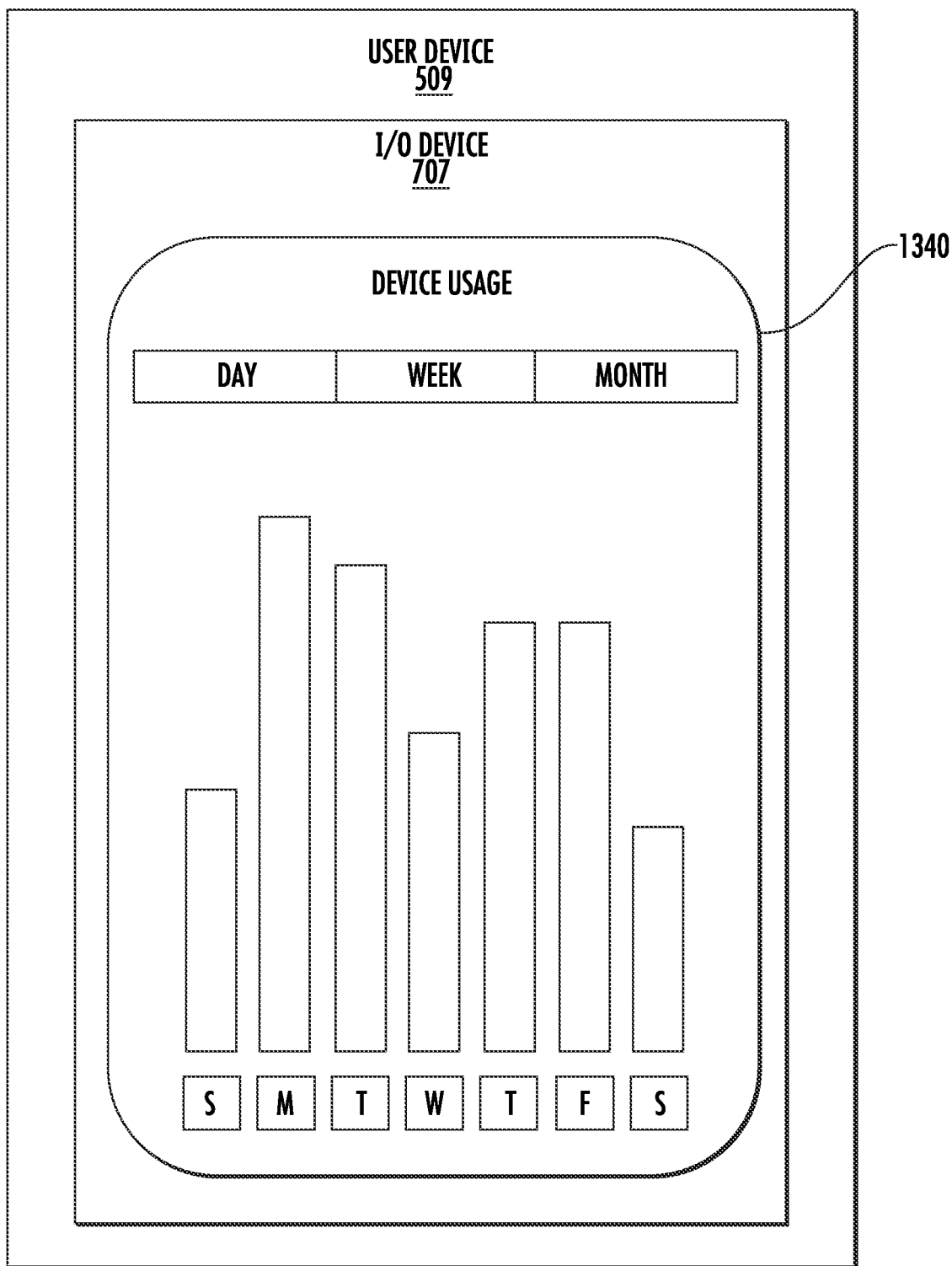
Figure 15F:
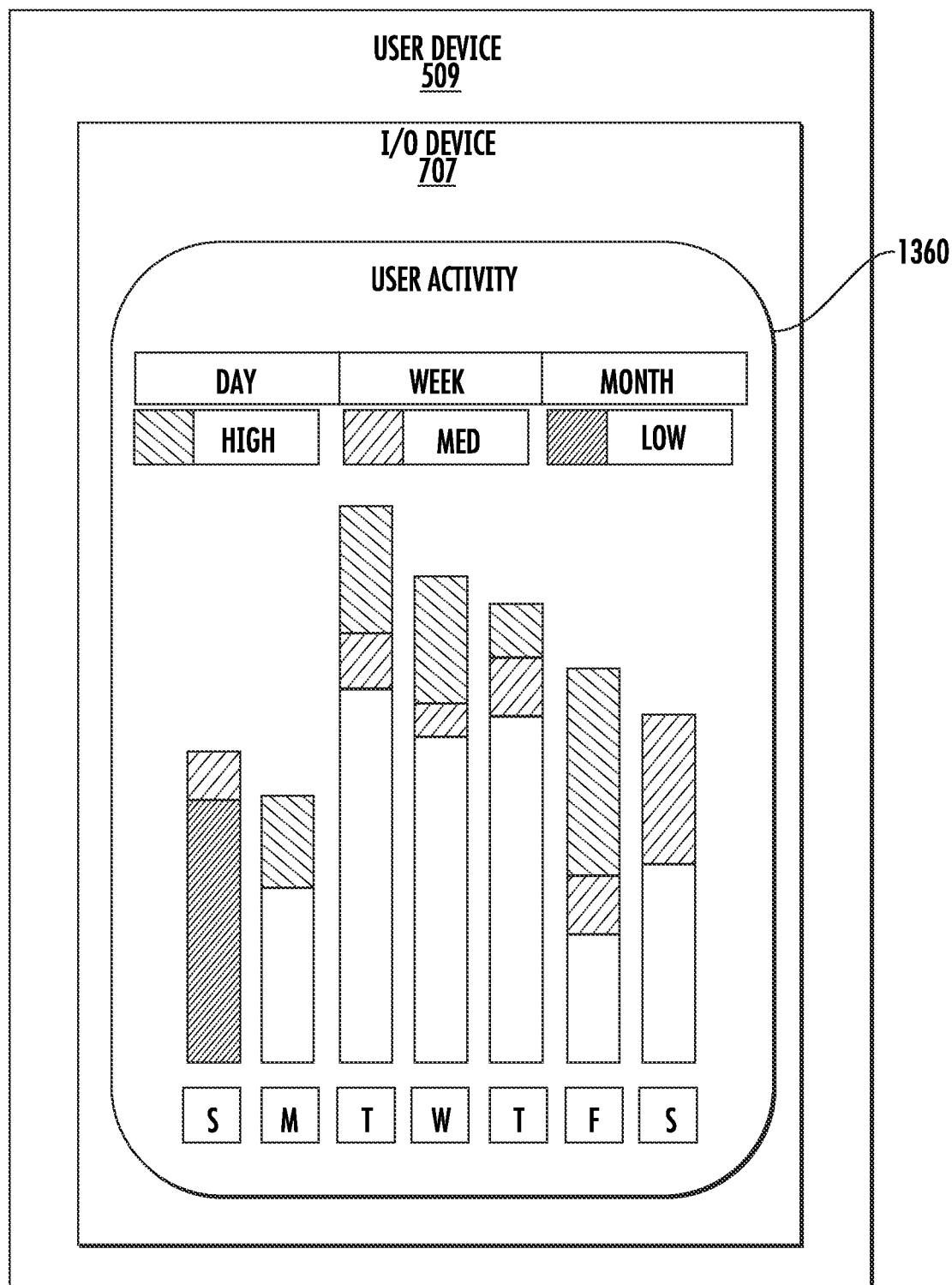
Figure 15G:
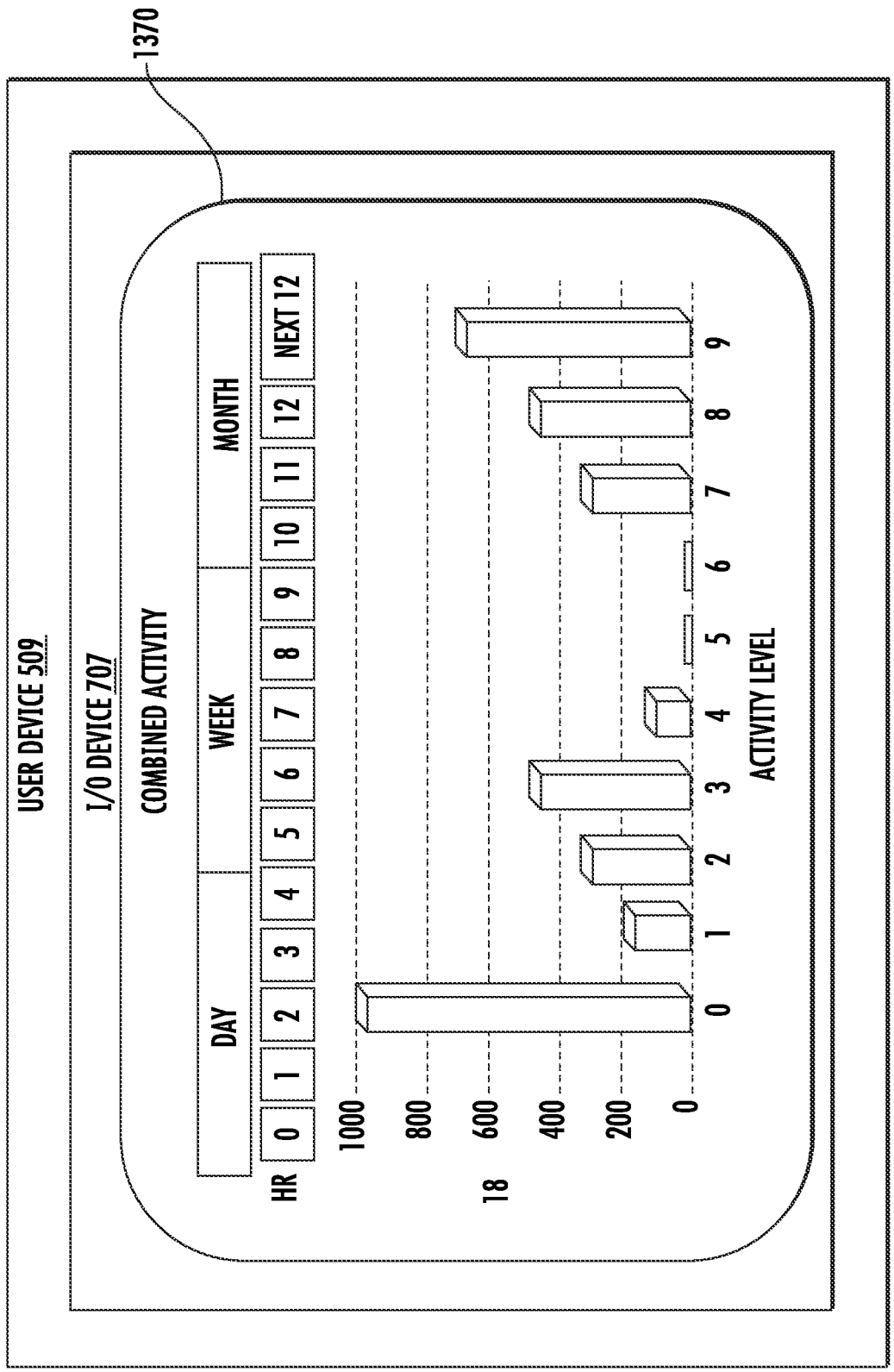

The reporting module 737 can be software, hardware, or a combination thereof that generates reports 529, stores the reports 529 in the data storage device 709, provides interactive user interfaces for selecting and displaying the reports 529 using the I/O interface 707, and communicate the reports 529 using the communications interface 717. The reporting module 737 can use predefined schema to collect, organize, and format the user status data 523, the activity data 545, the reference data 527 in portion, in full, and in combination to generate the reports 529. For example, FIGS. 15A to 15D illustrate examples of graphic user interfaces 1310, 1320, 1330, and 1331 provided on the I/O device 707 of the user device 509 providing selections for accessing and displaying reports of stimulation device usage 1332, user activity 1334, user status 1336, and combined information 1338. FIG. 15E illustrates an example graphic user interface 1340 displaying and example stimulation device usage report. FIG. 15F illustrates an example graphic user interface 1360 displaying and example user activity report based on data included in data digest 519 and the activity data 545. FIG. 15G illustrates an example graphic user interface 1370 displaying an example histogram of user activity based on data included in data digest 519 and the activity data 545. It is understood that the data can be displayed in other manners (e.g., line charts, pie charts, etc.). Further, it can combine and overlay the user status data 523, the activity data 545, the reference data 527 in various fashions.

Figure 10:
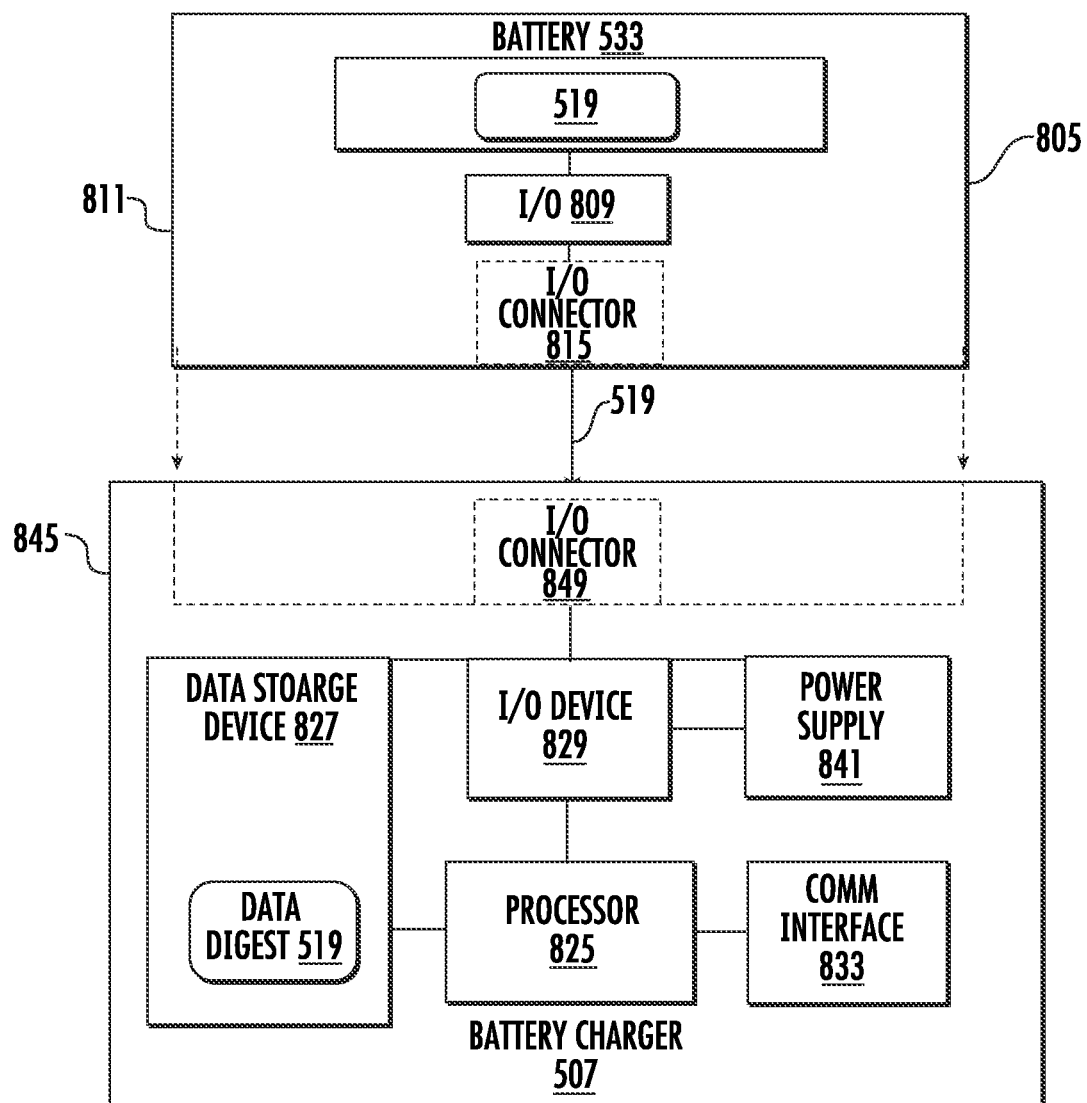
FIG. 10 shows a system block diagram illustrating an example of a battery and a battery charger.

FIG. 10 shows a system block diagram illustrating an example of a battery 533 and a battery charger 507, which can be the same or similar to those previously described above. The battery 533 can include a non-volatile data storage device 805, an input/output device 809, which can be the same or similar to those previously described herein. Additionally, the battery 533 can include a housing 811 and an input/output connector 815. The battery charger 507 can include a processor 825, non-volatile data storage device 827, an input/output device 829, and communications interface 833, which can be the same or similar to those previously described herein. Additionally, the battery charger 510 can include a power supply 841, a housing 845 and an input/output connector 849.

In some embodiments, the battery 533 connects to the battery charger 507 via input/output connectors 815 and 849. The battery 533 can receive power from the power supply 841 via the input/output connectors 815 and 849 and recharges the battery 533. Additionally, the battery 533 can provide data, such as data digest 519, stored in the data storage device 805 to the data storage device 527 of the battery charger 510 via input/output connectors 815 and 849 and I/O devices 809 and 829 under control of the processor 825. In some embodiments, the battery charger 507 can receive and mate with the battery 533. For example, the housing 811 of the battery 533 can be inserted in the battery charger 507 such that the connector 815 of the battery 533 mates with the connector 849 of the battery charger 507. It is understood that other methods and structures for connecting the battery charger 507 and the battery 533 can be used.

As illustrated above in FIG. 7, the battery 533 can also connect to a stimulation device (e.g., stimulation device 503) to receive and store the data digest 519. It is understood that the battery 533 can connect to the stimulation device in a similar manner as is described above regarding the battery charger 507. More specifically, the battery 533 can receive power from the power supply 841 via the input/output connectors 849 to a corresponding connector of the user device and power the user device. The battery 533 can store the data digest 519 in the data storage device 505 via input/output connectors 815 and the I/O device 809 under control of a processor (e.g., processor 612) of the stimulation device.

Figure 11:
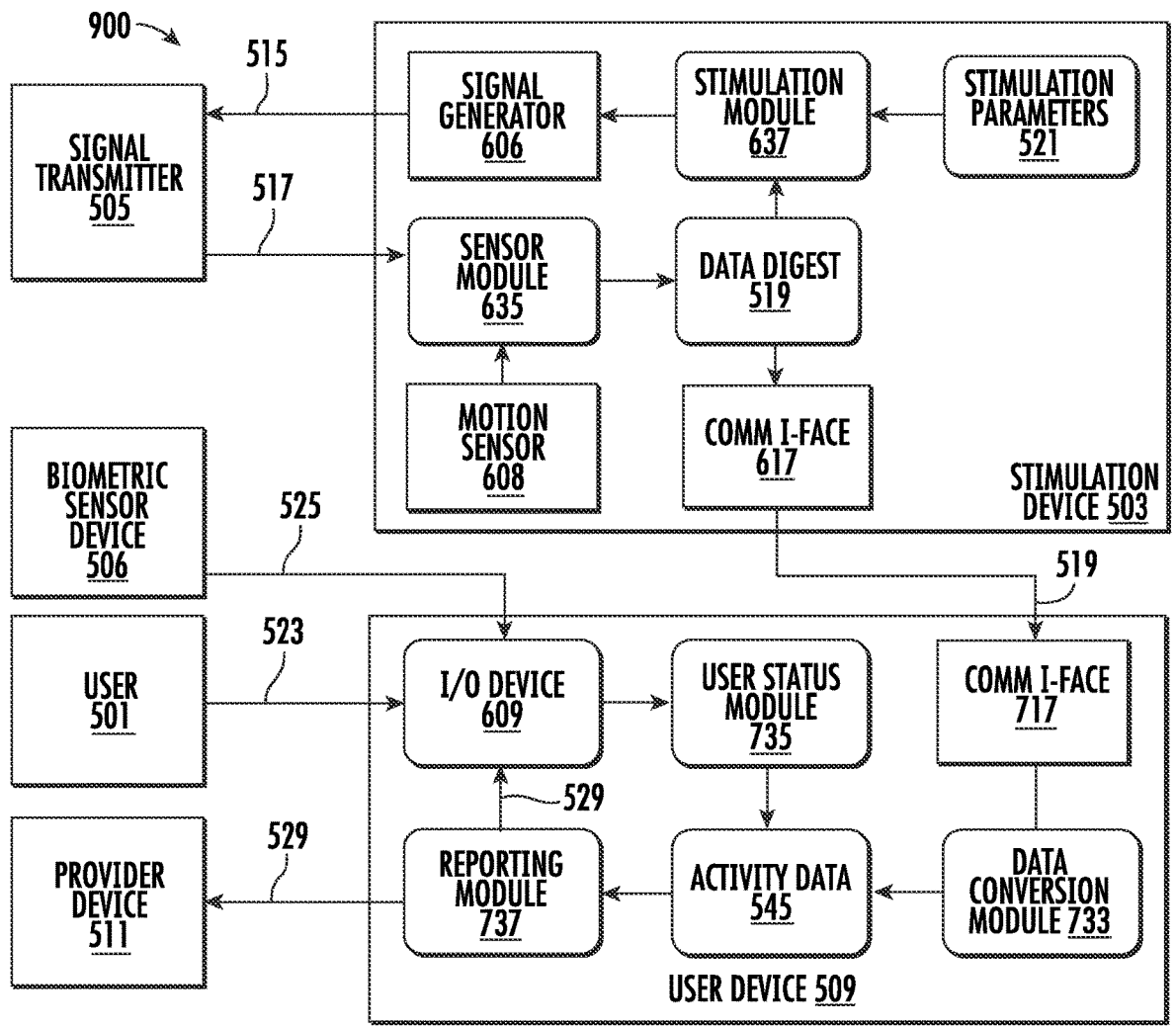
FIG. 11 shows a functional flow block diagram of an example of a system.

FIG. 11 shows a functional flow block diagram illustrating an example of a process 900 performed by a system. The process 900 includes user 501, stimulation device 503, signal transmitter 505, biometric sensor device 506, user device 509, and provider device 511, all of which can be the same or similar to those previously described herein. The stimulation device 503 can be communicatively connected to the user 501 via the signal transmitter 505. The stimulation module 637 can control the signal generator 606 to generate the stimulation signal 515 based on the stimulation parameters 521. The signal parameters 521 can be stored in the user device 509 (e.g., in storage device 610). In some embodiments, the stimulation parameters 521 can be provided to the stimulation device 503 by the user device 509.

The signal transmitter 505 can apply the stimulation signal 515 transcutaneously through the skin of the user 501 to the target treatment site (e.g., joint, muscle, nerve, bone, ligament, vasculature, and/or other hard or soft tissue, etc.) Additionally, the signal transmitter 505 can provide an impedance signal 517 representing a measurement of impedance to a flow of electrical current across the skin of the user 501 to the sensor module 635. The sensor module 635 can generate impedance information by conditioning the impedance signal 517, periodically sampling it, and storing timestamped values of the samples in the data digest 519. In some embodiments, the stimulation module 637 controls the signal generator 606 to modify the stimulation signal 515 based on the impendence data stored in the data digest 519 to account for changes in impedance in the user's skin over time.

Further, the biometric sensor device 506 and the motion sensor 608 can detect physical parameters of the user 501 and provide motion data and biometric data 525 to the user device 509. In some embodiments, the sensor module 635 can condition the motion data and the biometric data 525 received from the biometric sensor device 506 and the motion sensor 608, periodically sample them, and store timestamped values of the samples in the data digest 519. It is understood that, in some embodiments, the motion data and the biometric data 525 can be provided as time stamped samples and the user device 509 can store the information directly in the data digest 519 without being sampled or modified by the sensor module 635.

The user device 509 can receive and store the data digest 519 generated by the stimulation device 503. In some embodiments, stimulation device 503 transmits the data digest 519 to the user device 509. For example, the communication interface 617 of the stimulation device 503 periodically transmits the data digest 519 to the communication interface 717 of the user device 509 (e.g., about every 12 hours). In some other embodiments, the stimulation device 503 asynchronously transmits the data digest 519 to the user device 509. In some other embodiments, as detailed above, a removable battery (e.g., battery 533) of the stimulation device 503 stores the data digest 519 and provides it to the user device 509 while recharging in a battery charger (e.g., battery charger 507).

Additionally, the user device 509 can receive the user status information 523 from the user via one or more of the input/output devices 609. In some embodiments, the input/output devices 609 can include a touchscreen user interface, and the user status module 735 can periodically prompt the user 501 to input information describing the user's current conditions, such as mood, pain level, and medications taken. For example, based on a predetermined medication schedule (e.g., included in reference data 527), the user status module 735 can initiate alerts and prompts for the user 501 to take medication and receive confirmation from the user 501 that the medication was taken. The user status module 735 can timestamp the user status information 523 and store it in activity data 545.

Using the information in the data digest 519, as well as user status information 523 from the user 501 and biometric data 535 from the biometric sensor device 506, the user device 509 can determine the activity data 545. The reporting module 737 can use the activity data 545 to generate the reports 529, which can indicate user activity levels over periods of time. The activity level reported 529 can include, for example, one or more histograms illustrating activity levels during individual hours of individual days throughout the user's treatment. The user device 509 can display the reports 529 to the user 501 using an input/output device (e.g., I/O device 707) and provide the reports to the provider device 511.

Further, the reporting module 737 can process the activity data 545 to determine correlations, identify trends, and generate reports 529. The reporting module 737 can output the reports to the input/output device 609 for display to the user 501 via user interface. In some embodiments, using the impedance data in the data digest 519, the reporting module 737 can determine the time and the duration of use of the signal transmitter 505 by the user 101. Further, in some embodiments, using the data from the motion sensor 608 and biometric sensor device 506, the reporting module 737 can determine timing, duration, and intensity of the user's 501 activity. Additionally, in some embodiment, the user device 509 can suggest diagnoses of other maladies based on the data from the motion sensor 608 and the biometric sensor device 506.

Figure 12:
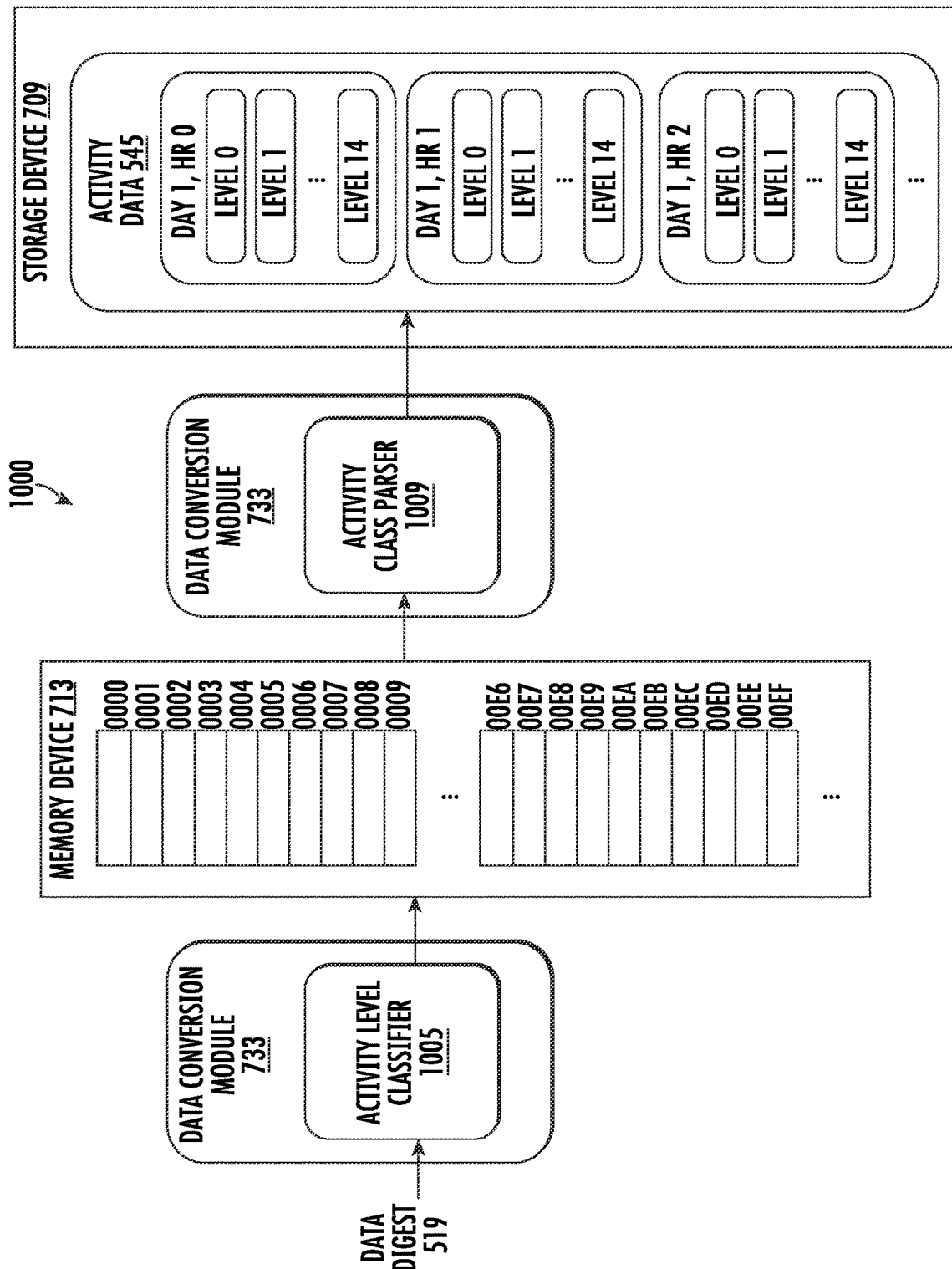
FIG. 12 shows a functional flow block diagram illustrating an example of process for determining activity data.

FIG. 12 shows a functional flow block diagram illustrating an example of a process 1000 for generating activity data 545. The process 1000 can use information contained in data digest 519, data conversion module 733, memory device 713, and storage device 709, all of which can be the same or similar to those previously described herein. The data conversion module 733 can include an activity level classifier 1005 and an activity class parser 1009. While the activity level classifier 1005 and the activity class parser 1009 are described as separate processing modules, it is understood that some or all of their functionality can be performed by a single module, such as the data conversion module 733, or their functionality can be divided among more modules.

As illustrated in FIG. 12, the activity level classifier 1005 can receive the data digest 519. As described previously, the data digest 519 can include time-indexed information recorded by a stimulation device (e.g., stimulation device 503). In some embodiments, the data digest 519 can include motion information generated by motion sensors (e.g., motion sensor 608 of the stimulation device 503) and impedance information indicating user application of a stimulation signal (e.g., stimulation signal 515) to a user (e.g., user 701). The information in the data digest 519 can be correlated with one another based on their respective timestamps.

In some embodiments, the activity level classifier 1005 determines levels of activity by sampling the data digest 519 during individual time frames, determining values of the samples for the individual time frames, and determining a corresponding activity level group (e.g., a corresponding bin) for the individual samples from a plurality of predetermined activity level groups including different respective ranges of motion values. For example, the data digest 519 can include information recorded once every second (e.g., 1 Hertz), as indicated by timestamps. For data in the digest 519 sampled over a first minute (e.g., 60 records) of the information in the data digest 519, the activity level classifier 1005 can determine the peak values of the data in the first minute and classify the first minute into one of a predetermined number of activity levels, and store the determined activity level in the memory device 713 at, for example, record 0000. For example, the activity level classifier 1005 can use 15 levels, including level 0, level 1, level 2 . . . level 14. Samples in level 0 can have values from zero to $1/15$th of the maximum possible value. Samples in level 1 can have values from $1/15$th to $2/15$th of the maximum, and so on up to level 14, which can include samples having values between $13/14$th to the maximum. Hence, if the sample for the first minute of the data digest 519 indicates zero activity, the activity level classifier 1005 can classify the first minute in the lowest activity level (e.g., level 0) and store the activity level in the memory device 713 in a respective r, such as record 0000. Whereas, if the sample for the first minute of the data digest 519 indicate extremely high activity, the activity level classifier 1005 can classify the first minute in the highest activity level (e.g., level 14) and store that activity level in the respective record. The activity level classifier 1005 can sample successive minutes of data in the data digest 519, determine the peak value of the data, and classify the individual samples into respective activity levels. Hence, at the end of a day, for example, all of a user's activity for individual minutes can be classified into one of the activity levels 0-14.

In a non-limiting example, the user may have performed activities over 50 seconds that are detected by a motion sensor and recorded in the data digest 519. The activity level classifier 1005 can sample the data including that activity in the data digest 519, determine a value of the data by converting the data to a vector, and determine a peak magnitude of the vector of the sample. The activity level classifier 1005 can determine that the peak magnitude of the vector was between $1/15$th and $2/15$th of the maximum vector possible, which can correspond to activity level 1 and store the determined level as a record (e.g., record 0000) in the memory device 713.

Figure 13:
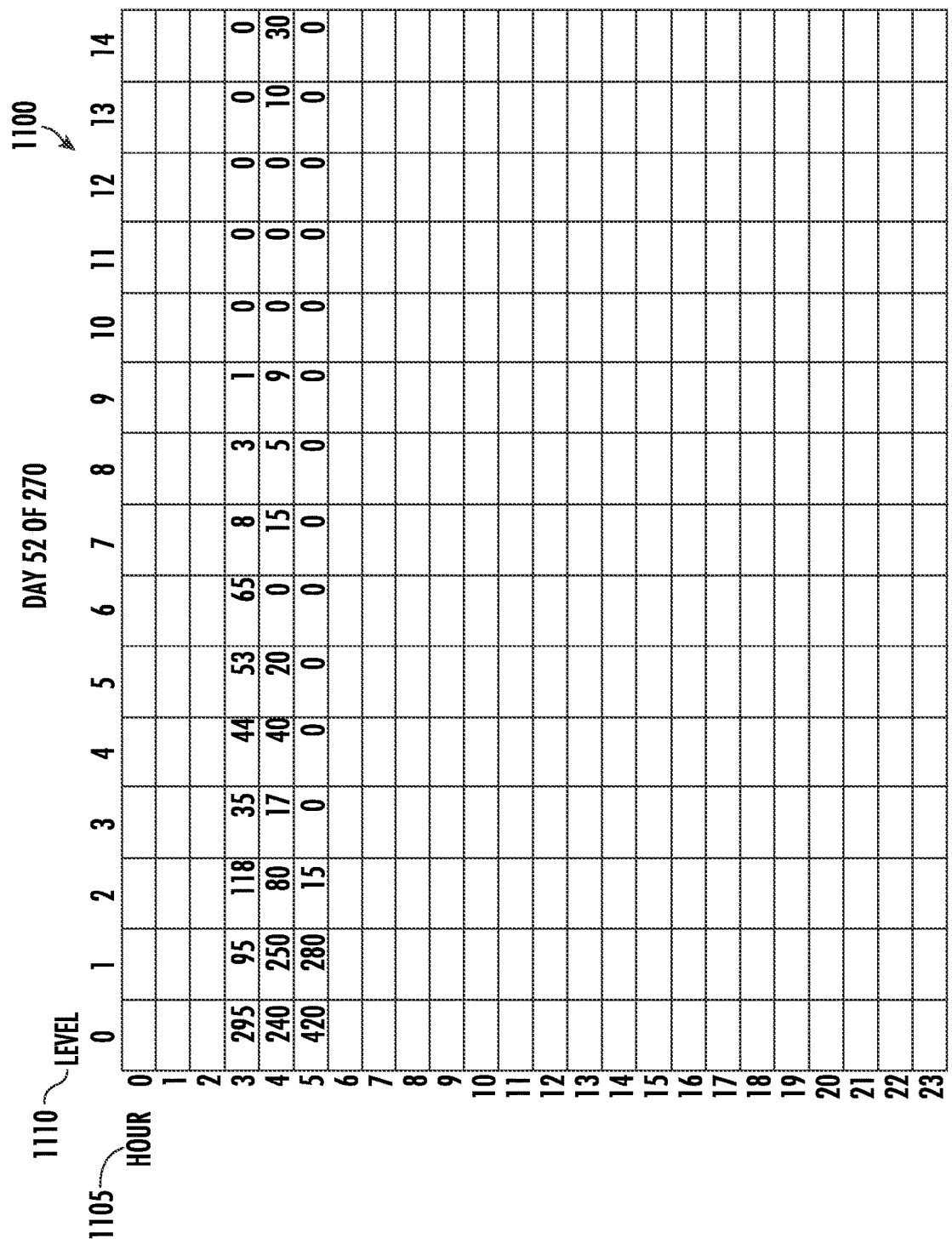
FIG. 13 shows a data structure illustrating example activity data determined.

Additionally, the activity class parser 1009 can parse samples into activity level groups for predetermined time periods (e.g., one hour time periods) based on their respective activity levels. For instance, the activity levels included in individual hours of the day (e.g., hours 0, 1, 2 . . . 23), the activity class parser 1009 can determine how many samples in the memory device 713 are classified in the individual the activity levels. For example, a first hour of a day (e.g., hour 0), which can include records 0000 to 003B in memory device 713, the activity class parser 1009 can determine a first quantity of the samples included in activity level group 0, a second quantity of samples included in activity level group 1, a third quantity of samples included in activity level group 2, and so on up to a fifteenth quantity of samples included in activity level group 14. For example, FIG. 13 shows a data structure 1100 containing activity data determined by the activity class parser 1009 using information contain in the memory device 713. The data structure 1100 can includes records associating individual hours 1105 (hours 0-23) of an individual day (e.g., day 52 of 270) with 15 activity levels 1110 (levels 0-14). For a fourth hour of the day (e.g., hour 3), the activity class parser 1009 can determine that the records 00F0 to 012B are stored in the memory device 713 include 295 samples in activity level group 0, a 95 samples included in activity level group 1, 118 samples included in activity level group 2, 35 samples included in activity level group 3, 44 samples included in activity level group 4, 53 samples included in activity level group 5, 65 samples included in activity level group 6, 8 samples included in activity level group 7, 3 samples included in activity level group 8, 1 sample included in activity level group 9, 0 samples included in activity level group 10, 0 samples included in activity level group 11, 0 samples included in activity level group 12, 0 samples included in activity level group 13, and 0 samples included in activity level group 14. Based on the samples determined to be in the individual activity level groups, the system can determine a quantity of time included in the activity levels within the time period.

Figure 14:
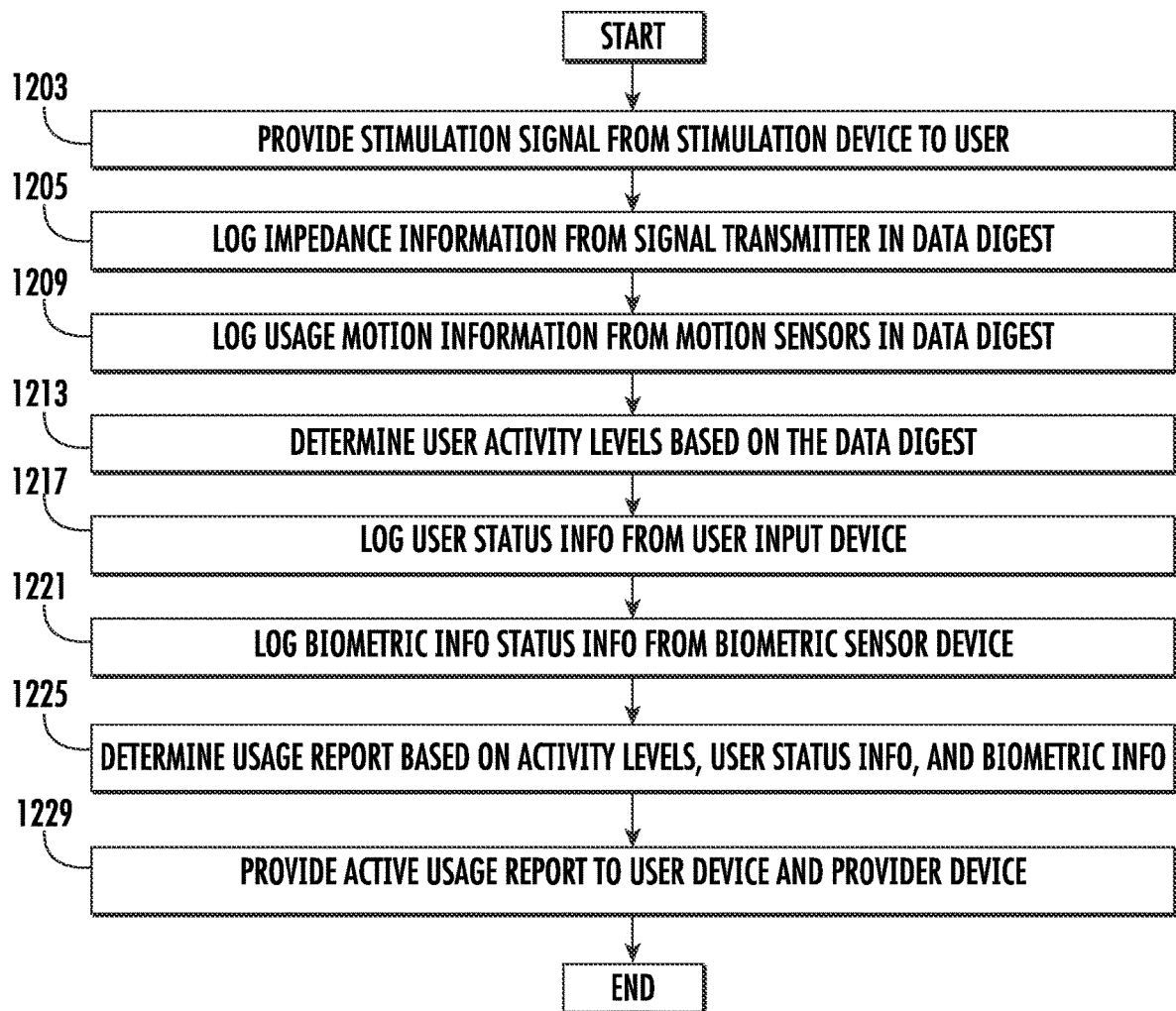
FIG. 14 shows a flow chart illustrating an example process performed by system.

The flow diagram in FIG. 14 illustrates an example of the functionality and operation of possible embodiments of systems, methods, and computer program products according to various embodiments described herein. The flow diagram can represent a module, segment, or portion of program instructions, which includes one or more computer executable instructions for implementing the illustrated functions and operations. In some alternative embodiments, the functions and/or operations illustrated in a particular block of the flow diagram can occur out of the order shown in FIG. 14. For example, two blocks shown in succession can be executed substantially concurrently, or the blocks can sometimes be executed in the reverse order, depending upon the functionality involved. It will also be noted that each block of the flow diagram and combinations of blocks in the block can be implemented by special purpose hardware-based systems that perform the specified functions or acts, or combinations of special purpose hardware and computer instructions.

At block 1203, the system (e.g., stimulation device 503 executing stimulation module 637) can output a therapeutic stimulation signal (e.g., stimulation signal 515) for a user (e.g., user 501). As detailed above, the system can generate the stimulation signal based on predetermined or dynamically determined parameters (e.g., stimulation parameters 521) using a signal generator (e.g., signal generator 606) via a signal transmitter (e.g., electrodes 40, 42 in signal transmitter 505).

At block 1205, the system (e.g., stimulation device 503 executing sensor module 635) can log impedance information from the signal transmitter. In some embodiments, the system can periodically determine magnitudes of samples of an impedance signal (e.g., impedance signal 517) output from the signal transmitter, timestamp the values of the samples, and store the timestamped impedance values in a data digest (e.g., data digest 519).

At block 1209, the system can log motion information from motion sensors (e.g., motion sensor 608) of the stimulation device. In some embodiments, the system can periodically determine values of samples of motion signals (e.g., magnitudes of acceleration vectors) output from the motion sensors, timestamp the values of the samples and store the timestamped motion values in the data digest in association with the impedance values logged at block 1205 based on their respective timestamps.

At block 1213, the system (e.g., user device 509 executing data conversion module 733) can determine the user's activity levels (e.g., activity data 545) based on the samples in the data digest. As previously described, determining the activity levels can include determining the values of the samples over individual time frames (e.g., one minute increments), determining the maximum value of the samples included in their respective time frames, and classifying the individual samples into one of a number of predetermined activity levels (e.g., one of levels 0-14) based on their respective maximum values. Determining the values of the samples can include converting values of the samples into vectors and determining the maximum magnitudes of the individual vectors. Based on the activity levels of the time frames, the system can create activity data by parsing the records into a plurality of groups based on their respective activity levels determined at block 1213 and determine the quantity activity levels records included in the individual groups, such as illustrated in FIG. 13.

At block 1217, the system (e.g., user device 509 executing user status module 735) can obtain user status information (e.g., user status data 523) from the user. As previously described above and illustrated in FIGS. 15B and 15C, the system can generate and display interactive user interfaces prompting the user to enter the user status information. Additionally, at block 1221, the system (e.g., user device 509 executing user status module 735) can obtain biometric information (e.g., biometric data 525) from the biometric sensor device (e.g., biometric sensor device 506).

At block 1225, the system (e.g., user device 509 executing user reporting module 737) can generate or determine one or more usage reports (e.g., reports 529) based on the activity levels determined at block 1213, the user status information logged at block 1217, and the biometric information logged at block 1221. In some embodiments, the report illustrates the activity levels and the usage levels as histograms, bar charts, line charts, pie charts, or the like. Further, in some embodiments, the reports may combine user status information, such as pain data, with the motion levels and the usage levels. For example, the active usage report can indicate a time-correlation between user pain and activity levels by superimposing user pain data over levels over activity illustrate in particular time frames (e.g., daily, weekly, or monthly). It is understood that other types of graphical representations of the information can be used. At block 1229, the system can provide the usage report determined at block 1225 to the user and to a monitor device (e.g., monitor device 111).

This description and the accompanying drawings illustrate exemplary embodiments and should not be taken as limiting, with the claims defining the scope of the present disclosure, including equivalents. Various mechanical, compositional, structural, and operational changes may be made without departing from the scope of this description and the claims, including equivalents. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or illustrated components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." In addition, where features or aspects of the disclosure are described in terms of Markush groups, those skilled in the art will recognize that the disclosure is also thereby described in terms of any individual member or subgroup of members of the Markush group.

What we claim is:

1. A therapeutic stimulation system for use after a surgical intervention on a patient, the system comprising:
   an energy source;
   a housing comprising a signal generator coupled to the energy source, wherein the signal generator is configured to generate a therapeutic signal and apply the therapeutic signal through a skin of the patient to a target site;
   a sensor coupled to the housing and configured to sense a physiological parameter of the patient; and
   a computer-readable program configured for downloading onto a device, the computer-readable program being configured to instruct the device to prompt a user, when the user is the patient, to enter patient status information and further being configured to compare the patient status information with the physiological parameter, wherein the patient status information comprises one or more patient reported outcome measures obtained after the surgical intervention has been completed.

2. The system of claim 1, wherein the one or more patient reported outcome measures comprises one or more of: level of post-interventional pain, mood, medication use, activity level, and amount of sleep.

3. The system of claim 1, wherein the physiological parameter includes one or more of: heart rate, heart rate variability, heart rhythm, blood pressure, blood oxygen, blood flow, body temperature, gaze, and gait.

4. The system of claim 1, wherein the sensor is a motion sensor configured to detect motion of the housing, and the physiological parameter comprises motion data.

5. The system of claim 1, further comprising a processor within the housing.

6. The system of claim 5, wherein the processor is configured to determine usage levels of the signal generator, and further wherein the usage levels are based on a period of time that the therapeutic signal is applied to the skin of the patient.

7. The system of claim 6, wherein the computer-readable program is configured to compare the patient status information with the usage levels.

8. The system of claim 5, wherein the processor is configured to determine a plurality of motion data obtained from the sensor over a time frame and to group the plurality of motion data into at least one parameter.

9. The system of claim 1, further comprising one or more electrodes coupled to the signal generator, wherein the energy source is configured to transmit one or more electrical impulses from the electrodes transcutaneously through the outer skin surface to a target location within a spine of the patient.

10. The system of claim 9, wherein the one or more electrical impulses are sufficient to enhance bone healing in the patient.

11. The system of claim 9, wherein the one or more electrical impulses have a frequency of about 50 kHz to about 70 kHz.

12. The system of claim 9, wherein the one or more electrical impulses have an amplitude of about 5 mA to about 10 mA.

13. The system of claim 1, wherein the computer-readable program is configured to compile the patient status information into an aggregate set of data.

14. The system of claim 1, wherein the computer-readable program is configured to compare the patient status information with the physiological parameter over a period of time, wherein the period of time is longer than 24 hours.

15. The system of claim 1, wherein the computer-readable program controls the device to prompt the patient to enter the patient status information a period of time after the signal generator has applied the therapeutic signal.

16. The system of claim 15, wherein the period of time is at least one hour.

17. The system of claim 1, wherein the device is wearable on the patient.

18. A therapeutic stimulation system for use after a surgical intervention on a patient, the system comprising:
   an energy source;
   a housing comprising a signal generator coupled to the energy source, wherein the signal generator is configured to generate a therapeutic signal and apply the therapeutic signal through a skin of the patient to a target site;
   a sensor coupled to the housing and configured to sense a physiological parameter of the patient; and
   a computer-readable program configured for downloading onto a device, the computer-readable program being configured to instruct the device to prompt the patient to enter a level of post-intervention pain of the patient after the surgical intervention has been completed, and further being configured to compare the level of post-intervention pain with the physiological parameter.

19. The system of claim 18, wherein the device is wearable on the patient.

* * * * *